(12) United States Patent
Liu et al.

(10) Patent No.: US 11,390,598 B2
(45) Date of Patent: Jul. 19, 2022

(54) DIAMINE COMPOUND WITH MELDRUM'S ACID GROUP AND RELATED POLYMER THEREOF

(71) Applicant: National Tsing Hua University, Hsinchu (TW)

(72) Inventors: Ying-Ling Liu, Hsinchu (TW); Chien-Ho Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 441 days.

(21) Appl. No.: 16/720,488

(22) Filed: Dec. 19, 2019

(65) Prior Publication Data

US 2021/0061782 A1     Mar. 4, 2021

(30) Foreign Application Priority Data

Aug. 29, 2019 (TW) .................. 108131113

(51) Int. Cl.
  *C07D 319/06* (2006.01)
  *C08G 73/06* (2006.01)
  *C08G 73/10* (2006.01)
  *C08G 69/08* (2006.01)

(52) U.S. Cl.
  CPC ........... *C07D 319/06* (2013.01); *C08G 69/08* (2013.01); *C08G 73/06* (2013.01); *C08G 73/1067* (2013.01)

(58) Field of Classification Search
  CPC ....... C08G 73/10; C08G 69/08; C09D 179/00
  See application file for complete search history.

(56) References Cited

U.S. PATENT DOCUMENTS

| 7,146,909 B2 * | 12/2006 | Oohashi | .................. B41C 1/10 |
| | | | 101/453 |
| 2005/0256313 A1 | 11/2005 | Norenberg et al. | |
| 2006/0016356 A1 | 1/2006 | Oohashi et al. | |

FOREIGN PATENT DOCUMENTS

| CN | 1675187 A | 9/2005 |
| HU | 225528 | * 7/1997 |

OTHER PUBLICATIONS

Wu etal Utilization of a Meldrum's acid towards functionalized fluoropolymers possessing dual reactivity for thermal crosslinking and post-polymerization modification, Chem. Commun., 2015, 51, 9220-9222, published on Apr. 2015.*
USPTO strucure search, Apr. 2022.*

* cited by examiner

*Primary Examiner* — Gregory Listvoyb
(74) *Attorney, Agent, or Firm* — The Webb Law Firm

(57) ABSTRACT

The present disclosure provides a diamine compound, which includes a structure represented by formula (I). Formula (I) is defined as in the specification. The present disclosure further provides an amide bond-containing polymer, a polyimide, a polybenzoxazine, a thermosetting resin and a copolymerized thermosetting resin prepared by the diamine compound including the structure represented by formula (I).

10 Claims, 35 Drawing Sheets
(1 of 35 Drawing Sheet(s) Filed in Color)

DIAMINE COMPOUND WITH MELDRUM'S ACID GROUP AND RELATED POLYMER THEREOF

CROSS-REFERENCE TO RELATED APPLICATION

This application claims priority to Taiwanese Patent Application No. 108131113 filed Aug. 29, 2019, the disclosure of which is hereby incorporated by reference in its entirety.

BACKGROUND

Technical Field

The present disclosure relates to a diamine compound and related polymer thereof. More particularly, the present disclosure relates to a diamine compound, an amide bond-containing polymer material, a polyimide, a polybenzoxazine, a thermosetting resin and a copolymerized thermosetting resin with a Meldrum's acid group.

Description of Related Art

Nowadays, the polymers have been widely used in the semiconductor industry, the automotive industry, the photoelectric industry, the biomedical materials, and the communication materials. Therefore, in the field of the polymers, the functional polymers having higher physical properties are more and more need, the physical properties such as the heat tolerance, the chemical resistance, the plasticity, the low dielectric constant or the low dielectric loss.

In the most industries, the diamine compound is often used as the monomer and the precursor for synthesizing the polymer. Therefore, many inventions target the diamine compound, the different chemical groups or functional groups are introduced into the structure of the diamine compound to functionalize, and the polymer obtained by using the diamine compound as the monomer and the precursor is also functionalized.

Therefore, how to develop a novel diamine compound to perform the improvement of the polymer structure, so that the polymer is connected with the functional groups with different functions to obtain the high functional polymer materials, which is the goal of the relevant industry.

SUMMARY

According to one aspect of the present disclosure, a diamine compound is provided. The diamine compound includes a structure represented by formula (I):

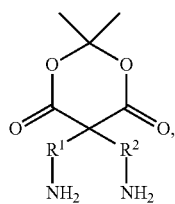

formula (I)

wherein $R^1$ and $R^2$ are the same or different from each other, and each independently an ether group, an ester group, an amine group or other heteroatom chain, a substituted or an unsubstituted alkyl group of 1 to 60 carbon atoms, a substituted or an unsubstituted alkenyl group of 2 to 60 carbon atoms, a substituted or an unsubstituted alkynyl group of 2 to 60 carbon atoms, a substituted or an unsubstituted aryl group of 6 to 30 carbon atoms or other carbon chain.

According to another aspect of the present disclosure, an amide bond-containing polymer material is provided. The amide bond-containing polymer material is prepared by a ring-opening self-polymerization of the diamine compound according to the aforementioned aspect.

According to further another aspect of the present disclosure, a polyimide is provided. The polyimide is prepared by a condensation reaction of the diamine compound according to the aforementioned aspect and a dianhydride monomer.

According to still another aspect of the present disclosure, a polybenzoxazine is provided. The polybenzoxazine is prepared by a condensation reaction of the diamine compound according to the aforementioned, a diphenol monomer and polyoxymethylene.

According to yet another aspect of the present disclosure, a thermosetting resin is provided. The thermosetting resin is prepared by self-crosslinking of the diamine compound according to the aforementioned.

According to further another aspect of the present disclosure, a copolymerized thermosetting resin is provided. The copolymerized thermosetting resin is prepared by adding the diamine compound according to the aforementioned to a thermosetting resin system.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Figure 1:
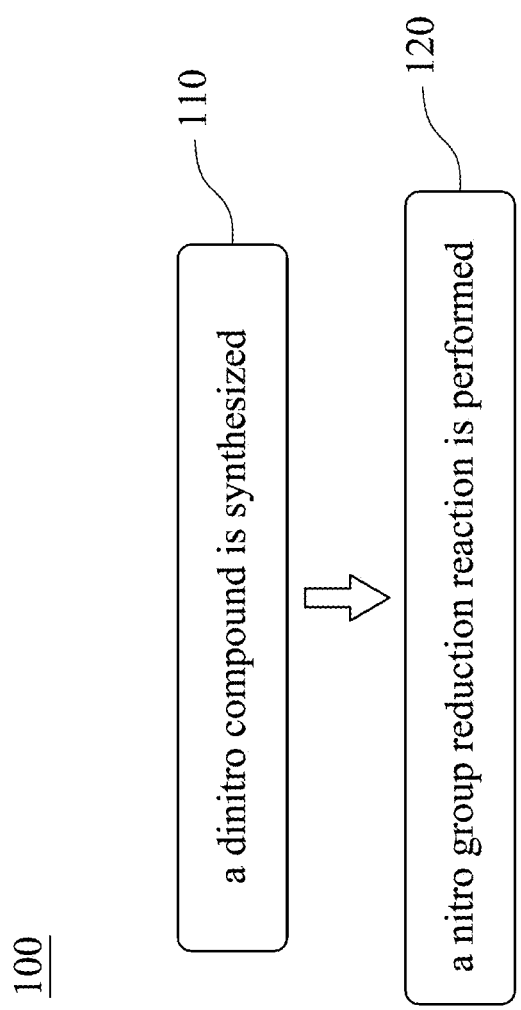
FIG. 1 is a flow chart of a manufacturing method for a diamine compound according to one embodiment of the present disclosure.

The present disclosure will be further exemplified by the following specific embodiments. However, the embodiments can be applied to various inventive concepts and can be embodied in various specific ranges. The specific embodiments are only for the purposes of description, and are not limited to these practical details thereof.

In the present disclosure, the compound structure can be represented by a skeleton formula, and the representation can omit the carbon atom, the hydrogen atom and the carbon-hydrogen bond. In the case that the functional group is depicted clearly in the structural formula, the depicted one is preferred.

In the present disclosure, in order to concise and smooth, "diamine compound includes a structure represented by formula (I)" can be represented as a diamine compound represented by formula (I) or a diamine compound (I) in some cases, and the other compounds or groups can be represented in the same manner.

A Diamine Compound

A diamine compound is provided of the present disclosure, which includes a structure represented by formula (I):

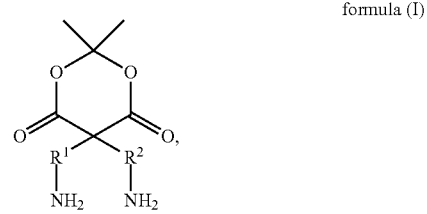

formula (I)

wherein $R^1$ and $R^2$ are the same or different from each other, and each independently an ether group, an ester group, an amine group or other heteroatom chains, a substituted or an unsubstituted alkyl group of 1 to 60 carbon atoms, a substituted or an unsubstituted alkenyl group of 2 to 60 carbon atoms, a substituted or an unsubstituted alkynyl group of 2 to 60 carbon atoms, a substituted or an unsubstituted aryl group of 6 to 30 carbon atoms or other carbon chains.

The aforementioned "substituted" means that at least one hydrogen atom can be substituted by the monovalent group, and the monovalent group can be the alkyl group of 1 to 60 carbon atoms, the alkenyl group of 2 to 60 carbon atoms or the alkynyl group of 2 to 60 carbon atoms.

With the aforementioned structure, the diamine compound of the present disclosure has a Meldrum's acid structure. The Meldrum's acid structure can be performed a thermal cracking reaction to form a ketene group at a high temperature, so as to perform a self-addition reaction and an addition reaction with a nucleophilic group. Therefore, by introducing the Meldrum's acid structure into the polymer structure, the reactivity of such a polymer can be polymerized, which is favorable for the subsequent crosslinking reaction and the modification reaction.

Furthermore, the diamine compound (I) can be used as a monomer and a precursor of the synthetic polymer. Thereby, the synthesized polymer can be performed the structural improvement by the Meldrum's acid structure, so that the polymer can connect with more functional groups with different functions. However, in the above polymerization reaction using the diamine compound (I) as a monomer, other monomers can be contained at the same time. The other monomers contain at least one reactive functional group, which can react with the amine group of the diamine compound to form the polymer. For example, the other monomers can be but are not limited to a dianhydride monomer or a diphenol monomer.

According to the aforementioned diamine compound (I), wherein, when $R^1$ and $R^2$ are benzyl groups in formula (I), which includes a structure represented by formula (I-AA):

formula (I-AA)

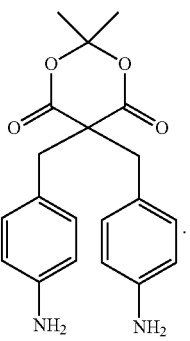

Hereafter, the manufacturing method for the diamine compound of the present disclosure and the synthesized polymer thereof are described by the diamine compound represented by formula (I-AA).

A Manufacturing Method for a Diamine Compound

Please refer to FIG. 1, which is a flow chart of a manufacturing method for a diamine compound 100 according to one embodiment of the present disclosure. Specifically, the manufacturing method for the diamine compound 100 can be used to prepare a diamine compound (I-AA). In FIG. 1, the manufacturing method for the diamine compound 100 includes a step 110 and a step 120.

In the step 110, a dinitro compound is synthesized, wherein a Meldrum's acid represented by formula (i) is reacted with 4-nitrobenzyl chloride represented by formula (ii) in the presence of potassium carbonate ($K_2CO_3$) at the room temperature for 72 hours to obtain a dinitro compound represented by formula (iii):

formula (i)

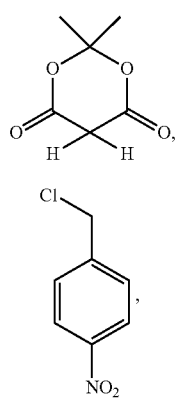

formula (ii)

formula (iii)

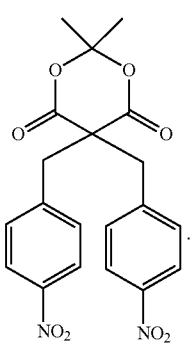

In the step 120, a nitro group reduction reaction is performed, wherein the dinitro compound represented by formula (iii) is reacted in the presence of stannous chloride ($SnCl_2·2H_2O$) at the room temperature for 24 hours, and then a nitro group is reduced to an amine group to obtain the diamine compound represented by formula (I-AA):

formula (I-AA)

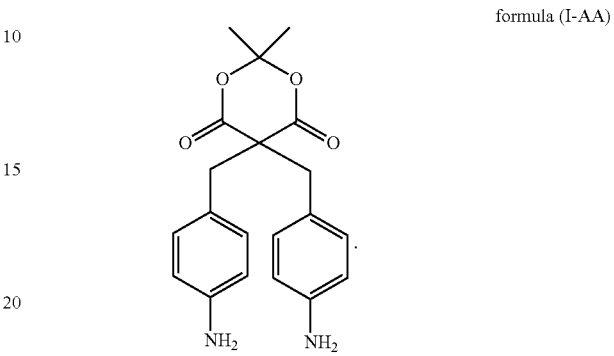

The reaction scheme of the manufacturing method for the diamine compound 100 is shown in Table 1.

TABLE 1

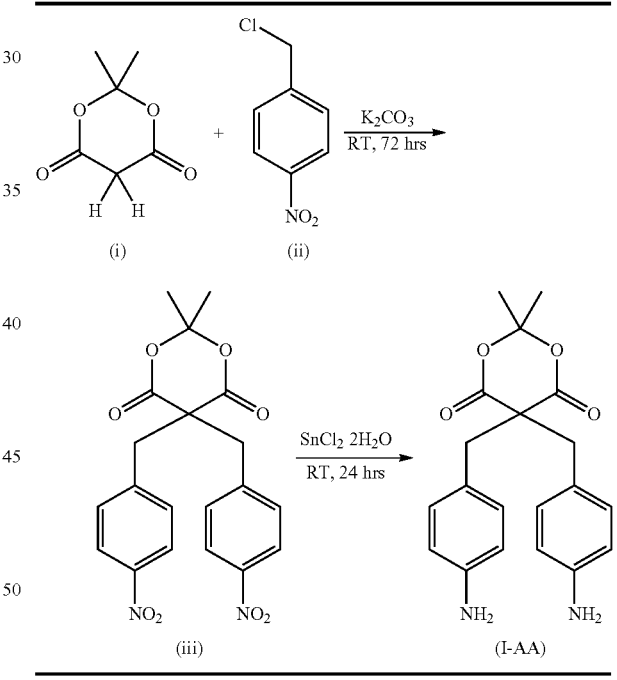

Amide Bond-Containing Polymer Material

An amide bond-containing polymer material is provided of the present disclosure, which is prepared by a ring-opening self-polymerization of the aforementioned diamine compound.

In detail, the amide bond-containing polymer material of the present disclosure is prepared by heating the diamine compound (I-AA), the Meldrum's acid structure is performed the thermal cracking reaction to form a ketene group, so that the ketene group can be reacted with the own amine group to self-polymerize into the amide bond-containing polymer material represented by formula (II). Specifically, the amide bond-containing polymer material represented by formula (II) is a polyamide polymer material.

The reaction process for synthesizing the polyamide polymer material (II) is shown in Table 2.

TABLE 2

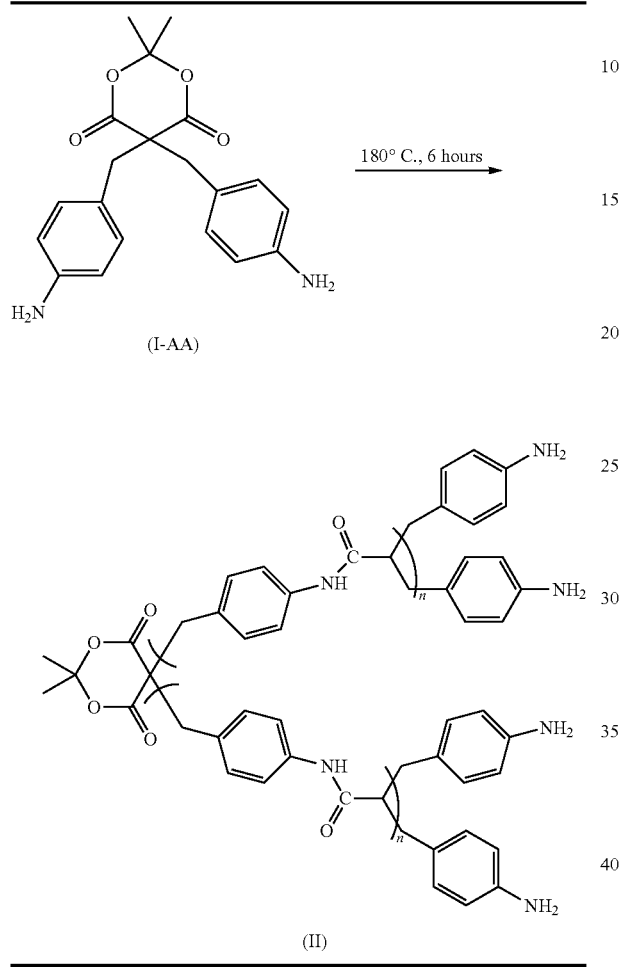

Polyimide

A polyimide is provided of the present disclosure, which is prepared by a condensation reaction of the aforementioned diamine compound and a dianhydride monomer. The dianhydride monomer includes a structure represented by formula (A):

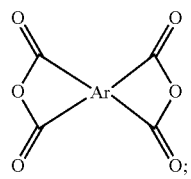

formula (A)

wherein Ar is a structure represented by formula (A-1), formula (A-2) or formula (A-3):

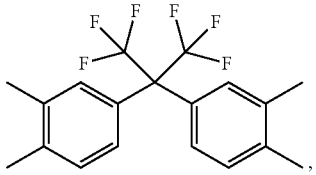

formula (A-1)

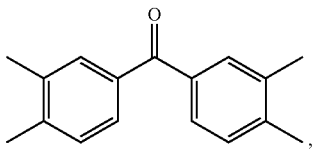

formula (A-2)

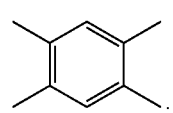

formula (A-3)

In detail, the polyimide of the present disclosure is prepared by the diamine compound (I-AA) and the dianhydride monomer represented by formula (iv) performed the ring opening reaction and the polyaddition reaction at the room temperature in the presence of N-methyl-2-pyrrolidinone (NMP) to form an intermediate product of a polyamic acid (PAA) represented by formula (v). Then, the polyamic acid represented by formula (v) is performed the condensation reaction at 100° C. in the presence of acetic anhydride (AcO$_2$) and pyridine (Py) to obtain the polyimide represented by formula (III). The dianhydride monomer (iv) is the structure that Ar is a structure represented by formula (A-1) in the dianhydride monomer (A).

The reaction process for synthesizing the polyimide (III) is shown in Table 3.

TABLE 3

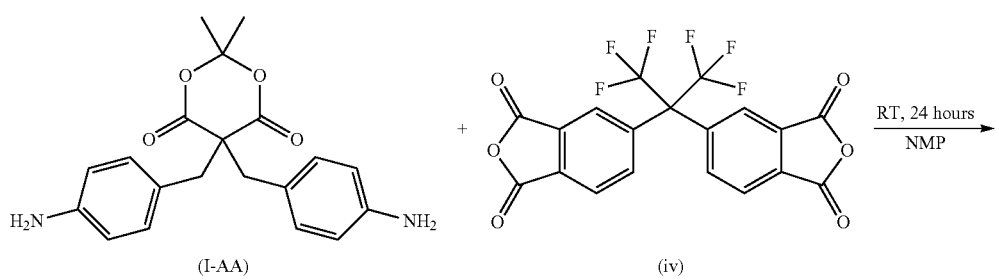

TABLE 3-continued

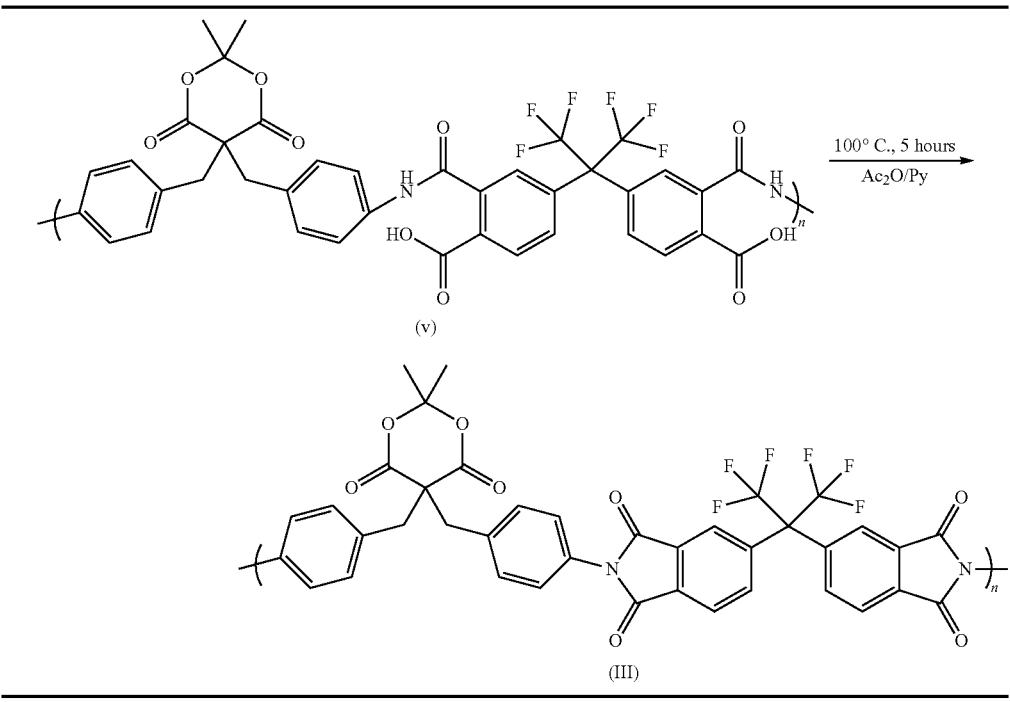

Polybenzoxazine

A polybenzoxazine is provided of the present disclosure, which is prepared by a condensation reaction of the aforementioned diamine compound, a diphenol monomer and polyoxymethylene. The diphenol monomer includes a structure represented by formula (B):

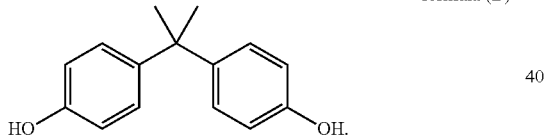

formula (B)

In detail, the polybenzoxazine of the present disclosure is prepared by the diamine compound (I-AA), the diphenol monomer represented by formula (B) and polyoxymethylene reacted at 80° C. for 72 hours to obtain the polybenzoxazine represented by formula (IV).

The reaction process for synthesizing the polybenzoxazine (IV) is shown in Table 4.

TABLE 4

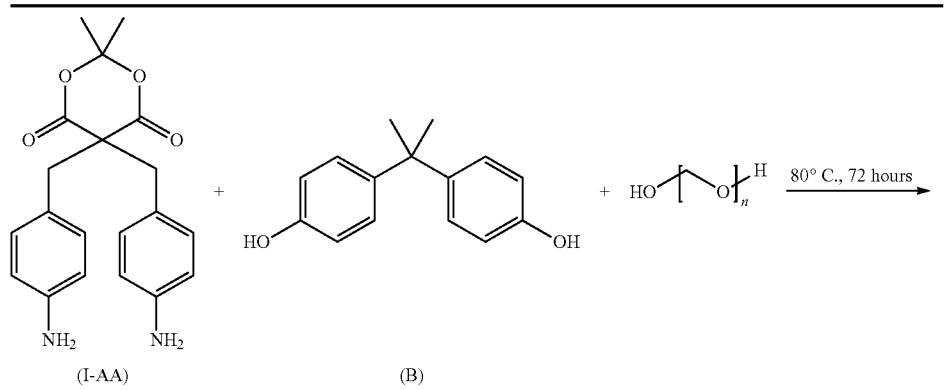

TABLE 4-continued

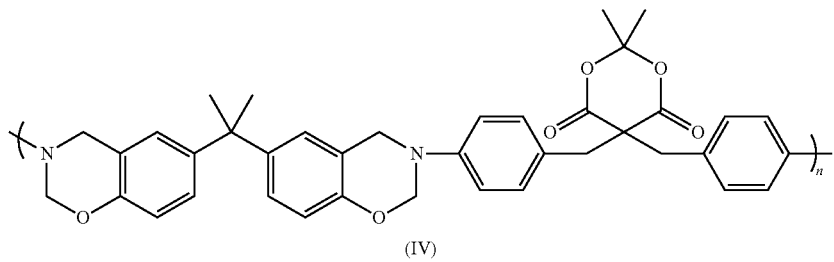

(IV)

Thermosetting Resin

A thermosetting resin is provided of the present disclosure, which is prepared by self-crosslinking of the aforementioned diamine compound. Further, the aforementioned diamine compound can be added to a thermosetting resin system to prepare a copolymerized thermosetting resin. The thermosetting resin system can be but is not limited to epoxy resin, phenolic resin, polyester resin, benzoxazine resin, carbamide resin or polyurethane resin.

Synthesis Example

Synthesis Example 1 of the present disclosure is a synthesis of a dinitro compound (iii). The synthesis method is to dissolve 2 g (13.88 mmole) of Meldrum's acid (i), 5.9523 g (34.69 mmole) of 4-nitrobenzyl chloride (ii) and 4.794 g (34.69 mmole) of potassium carbonate in 6 mL of dimthylformamide (DMF). After reacting for 72 hours at the room temperature, the above solution is neutralized with 1N of hydrochloric acid (HCl), and as a precipitate formed progressively. Then, ethyl acetate (EA) is added to extract non-reacted 4-nitrobenzyl chloride (ii), and collected the precipitate with filtration. Finally, the precipitate is dissolved in chloroform, and after removing impurity with filtration, a white dinitro compound (iii) is obtained with a yield of 70.3%. The reaction scheme of Synthesis Example 1 is shown below.

The reaction scheme of Synthesis Example 1

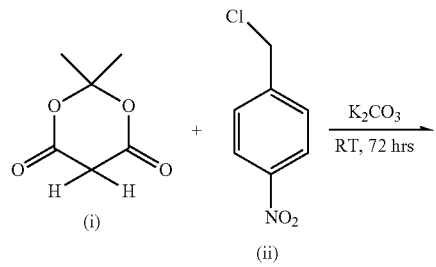

-continued

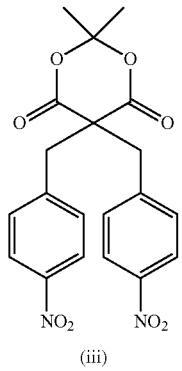

(iii)

Figure 2A:
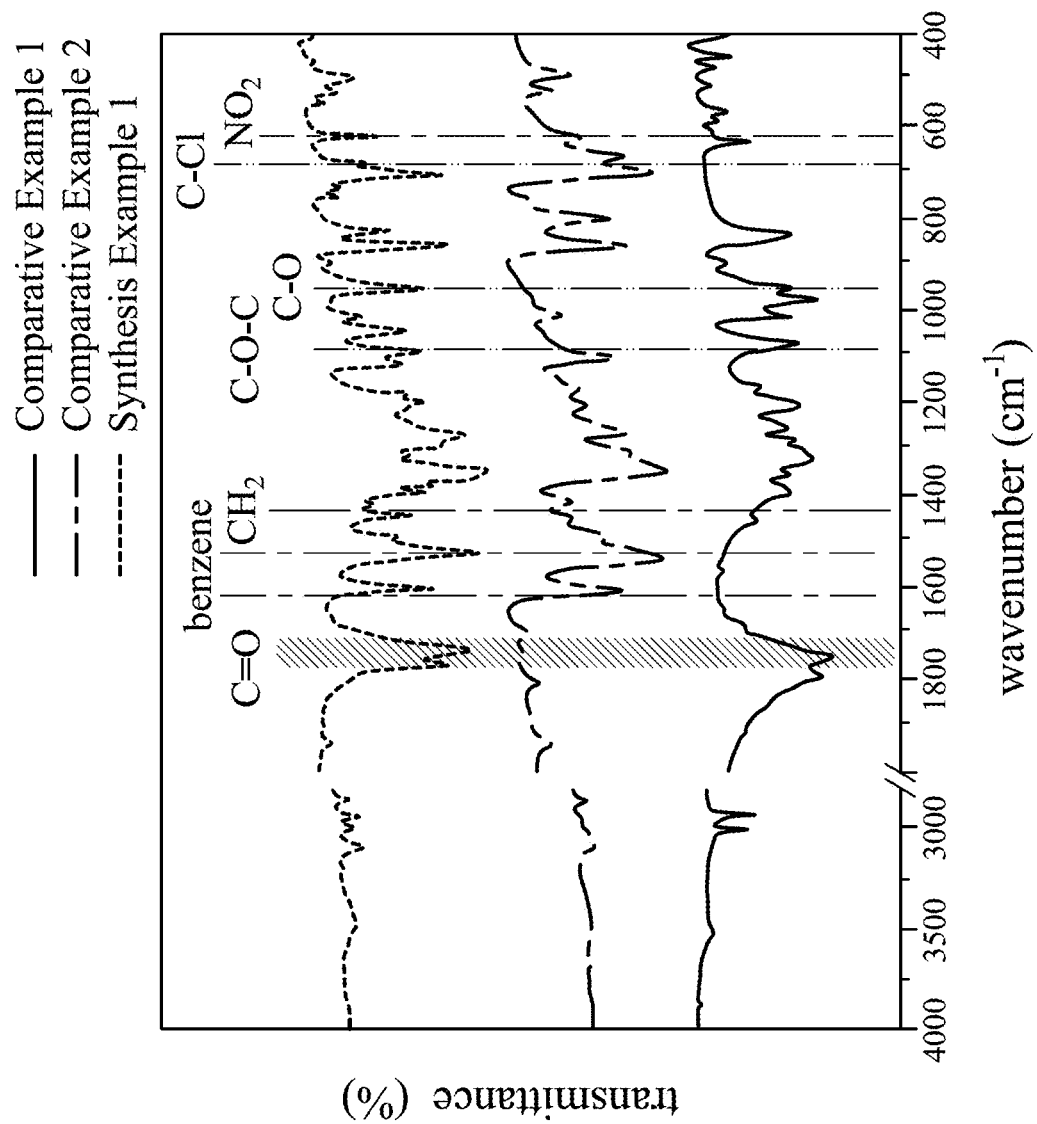
FIG. 2A is a FTIR spectrum of Comparative Example 1, Comparative Example 2, and Synthesis Example 1.
Figure 2B:
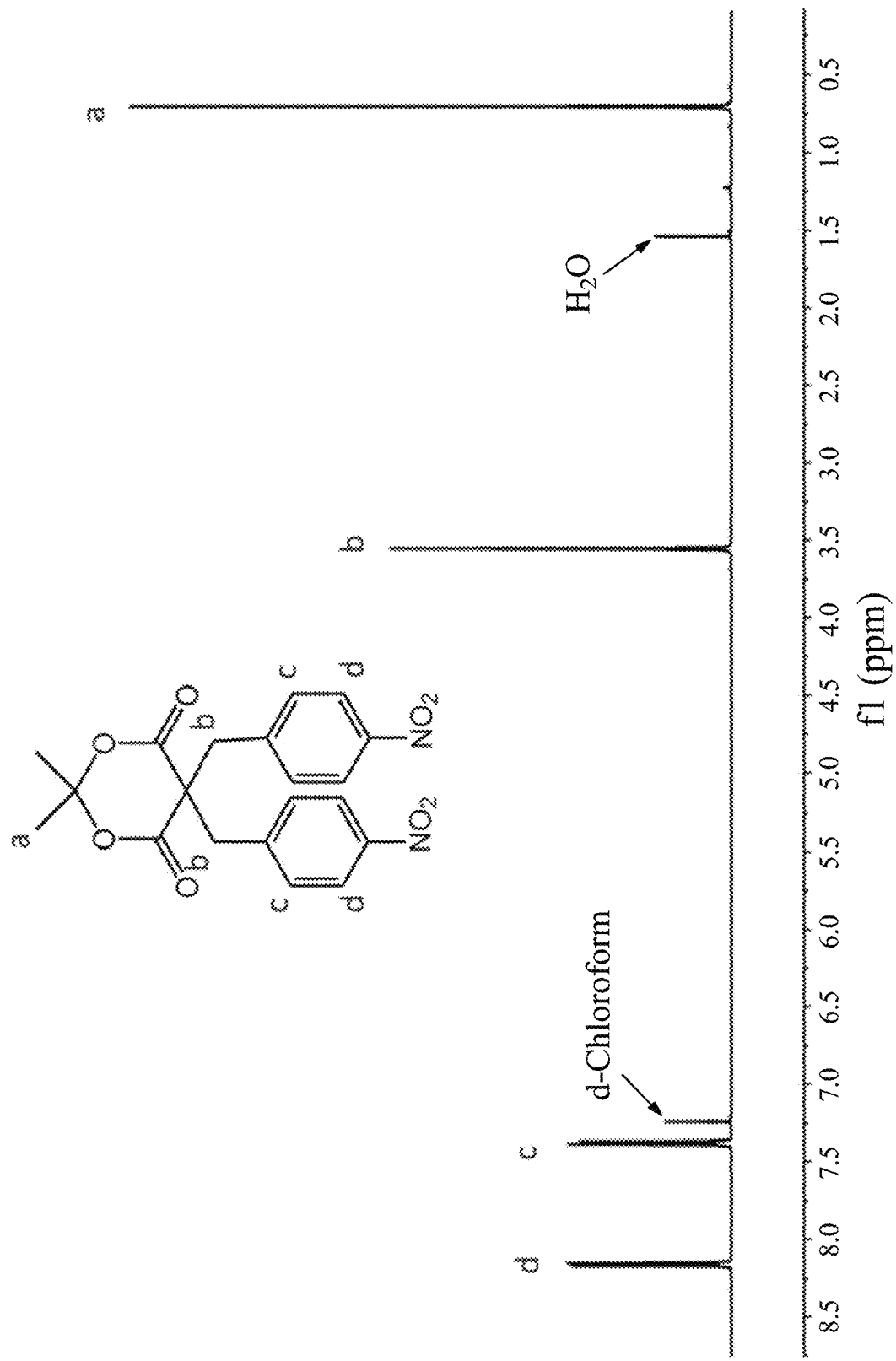
FIG. 2B is a $^1$H-NMR spectrum of Synthesis Example 1.
Figure 2C:
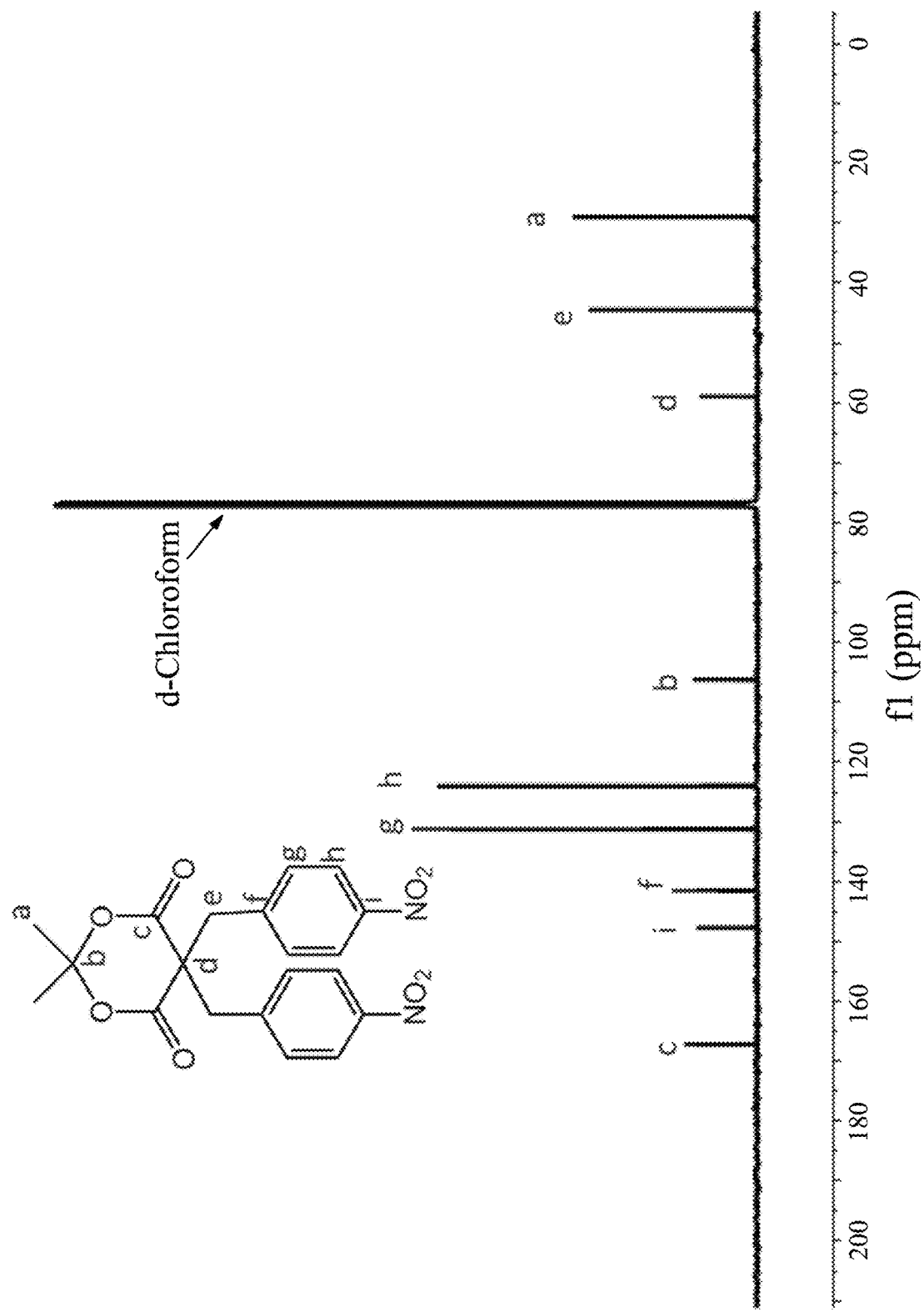
FIG. 2C is a $^{13}$C-NMR spectrum of Synthesis Example 1.
Figure 2D:
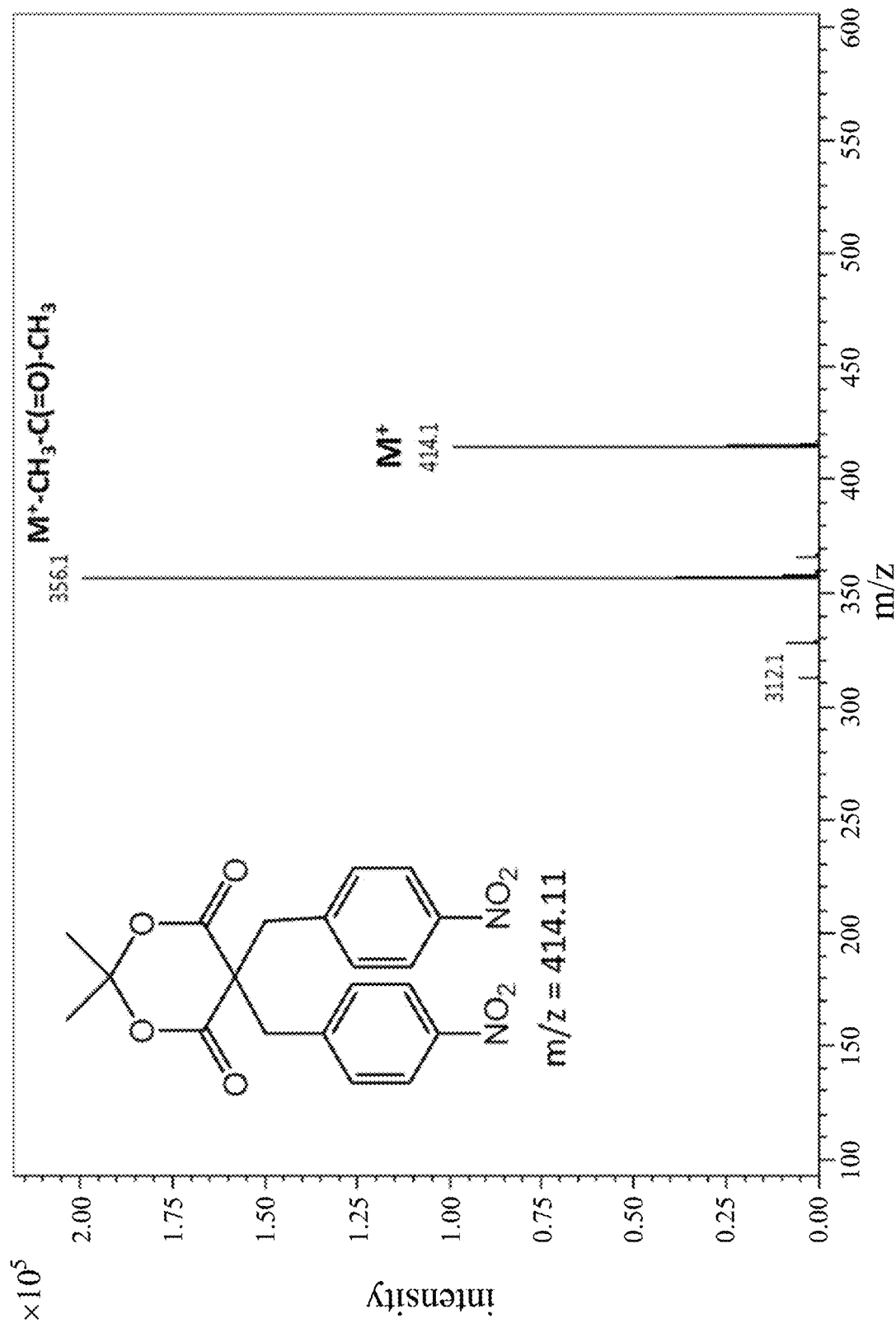
FIG. 2D is a mass spectrum of Synthesis Example 1.

Synthesis Example 1 is performed FTIR analysis, $^1$H-NMR analysis, $^{13}$C-NMR analysis, a mass spectrometry and an elemental analysis, so as to confirm the structure of Synthesis Example 1. Please refer to FIGS. 2A, 2B, 2C and 2D. FIG. 2A is a FTIR spectrum of Comparative Example 1, Comparative Example 2, and Synthesis Example 1. FIG. 2B is a $^1$H-NMR spectrum of Synthesis Example 1. FIG. 2C is a $^{13}$C-NMR spectrum of Synthesis Example 1. FIG. 2D is a mass spectrum of Synthesis Example 1. The result of the elemental analysis is shown in Table 5, wherein the analytical value 1 and the analytical value 2 are represented the results of the elemental analysis tested twice. The aforementioned Comparative Example 1 is Meldrum's acid (i), Comparative Example 2 is 4-nitrobenzyl chloride (ii). As known in FIGS. 2A to 2D, the product of Synthesis Example 1 is the dinitro compound (iii), and m/z is 414.11.

TABLE 5

|  | C(%) | H(%) | N(%) |
|---|---|---|---|
| analytical value 1 | 57.74 | 4.194 | 6.64 |
| analytical value 2 | 57.75 | 4.258 | 6.68 |
| theoretical value | 57.97 | 4.380 | 6.76 |

Example

Example 1 of the present disclosure is a diamine compound (I-AA). The synthesis method is to mix 5 g (12.068 mmole) of the dinitro compound (iii), 54.46 g (241.36 mmole) of stannous chloride, 100 mL of ethanol (EtOH) and 200 mL of tetrahydrofuran (THF) to form a solution. After the solution is reacted at the room temperature for 24 hours, most solvent is removed by a rotary evaporator, then the pH value is made slightly basic (pH=7-8) by adding 1N of sodium hydroxide (NaOH), and as a precipitate formed progressively. Then, extracting with ethyl acetate (EA) several times, and the aqueous phase is removed by adding magnesium sulfate (MgSO$_4$) to obtain the diamine compound (I-AA) with a yield of 65.4%. The reaction scheme of Example 1 is shown below.

The reaction scheme of Example 1

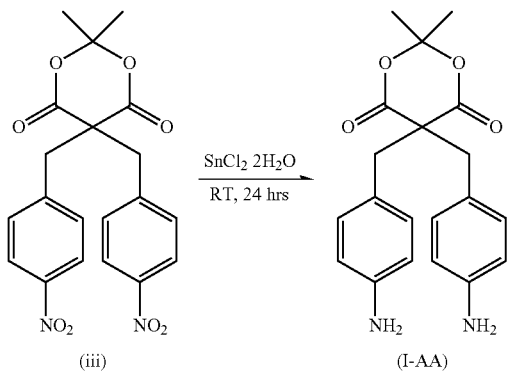

Figure 3A:
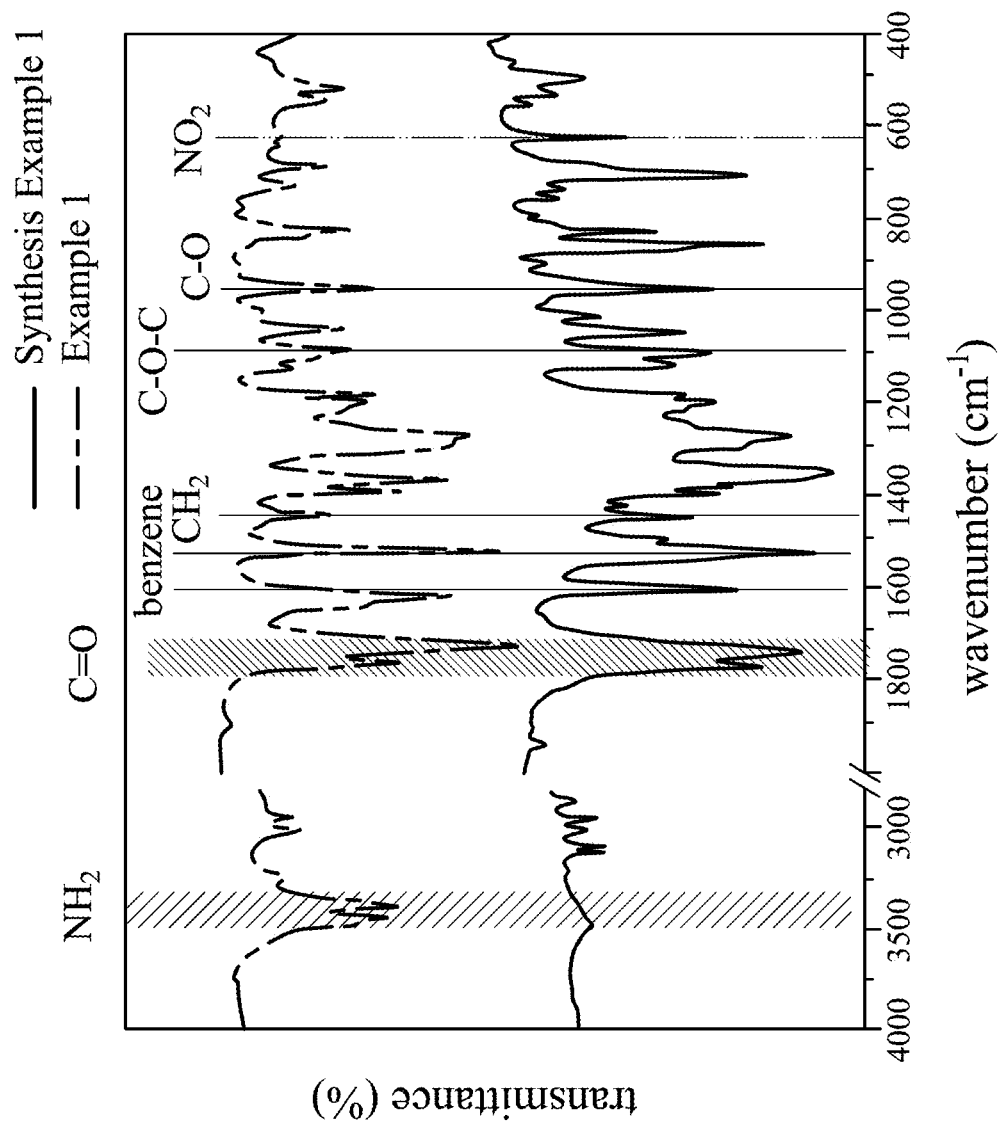
FIG. 3A is a FTIR spectrum of Synthesis Example 1 and Example 1.
Figure 3B:
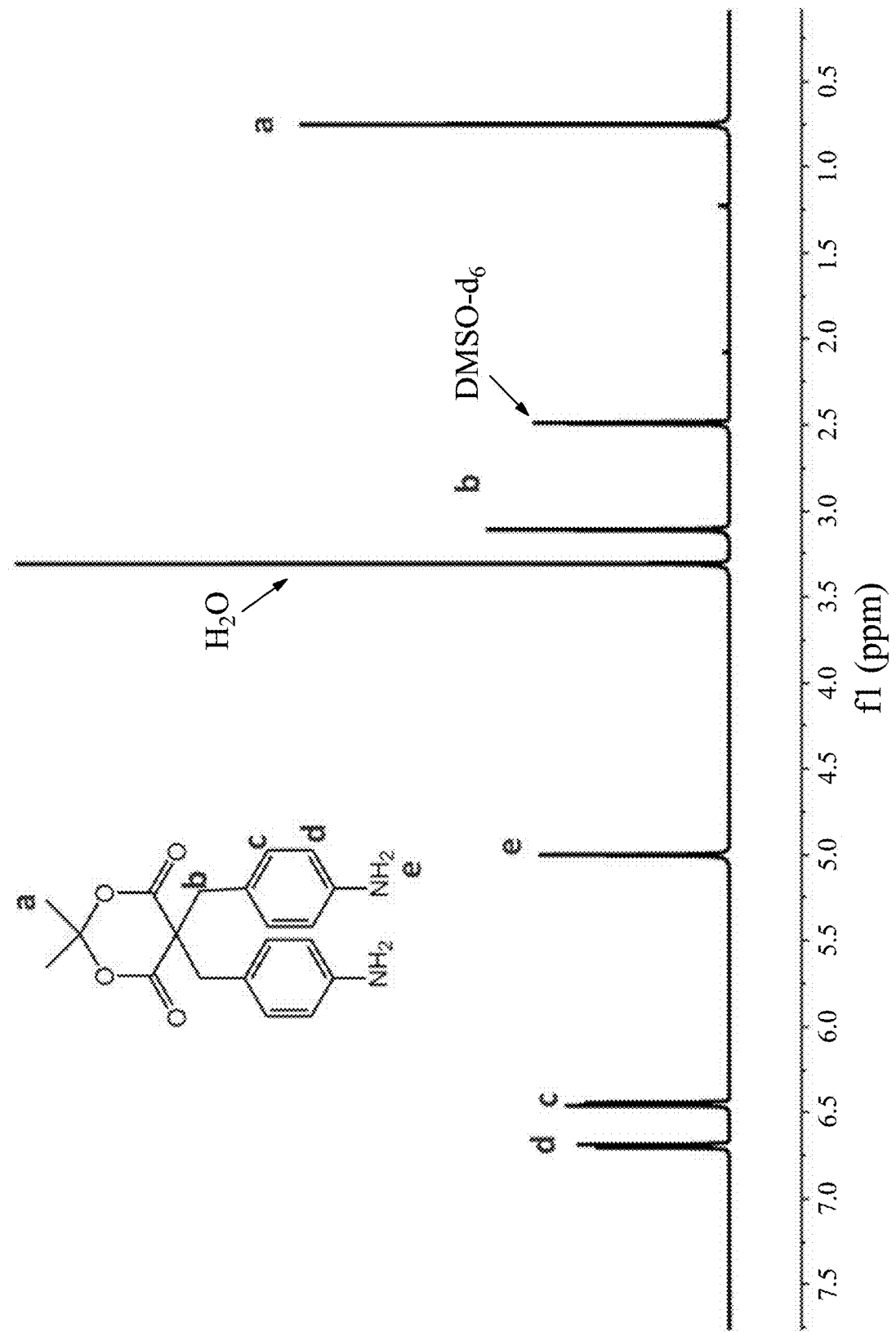
FIG. 3B is a $^1$H-NMR spectrum of Example 1.
Figure 3C:
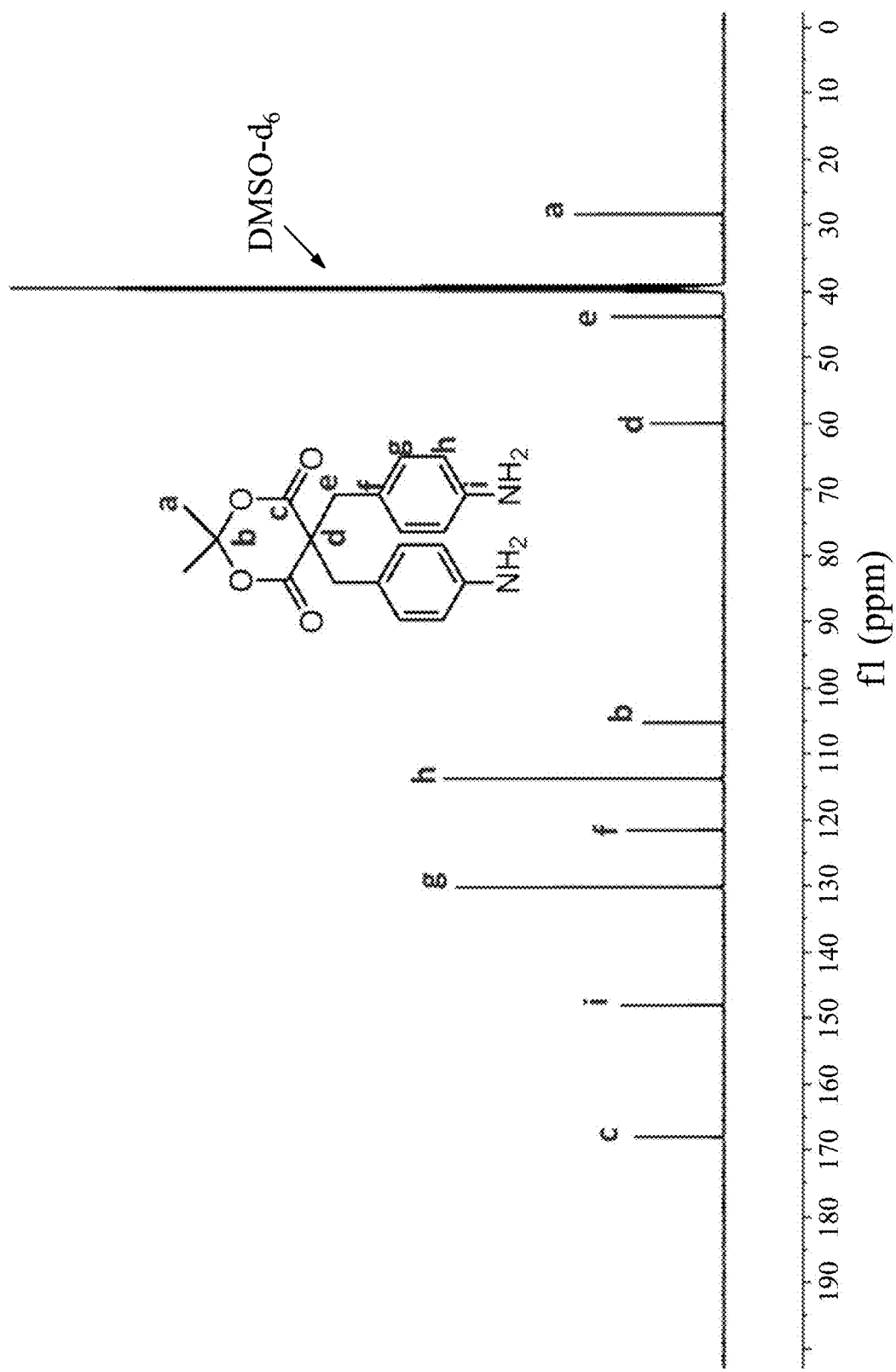
FIG. 3C is a $^{13}$C-NMR spectrum of Example 1.
Figure 3D:
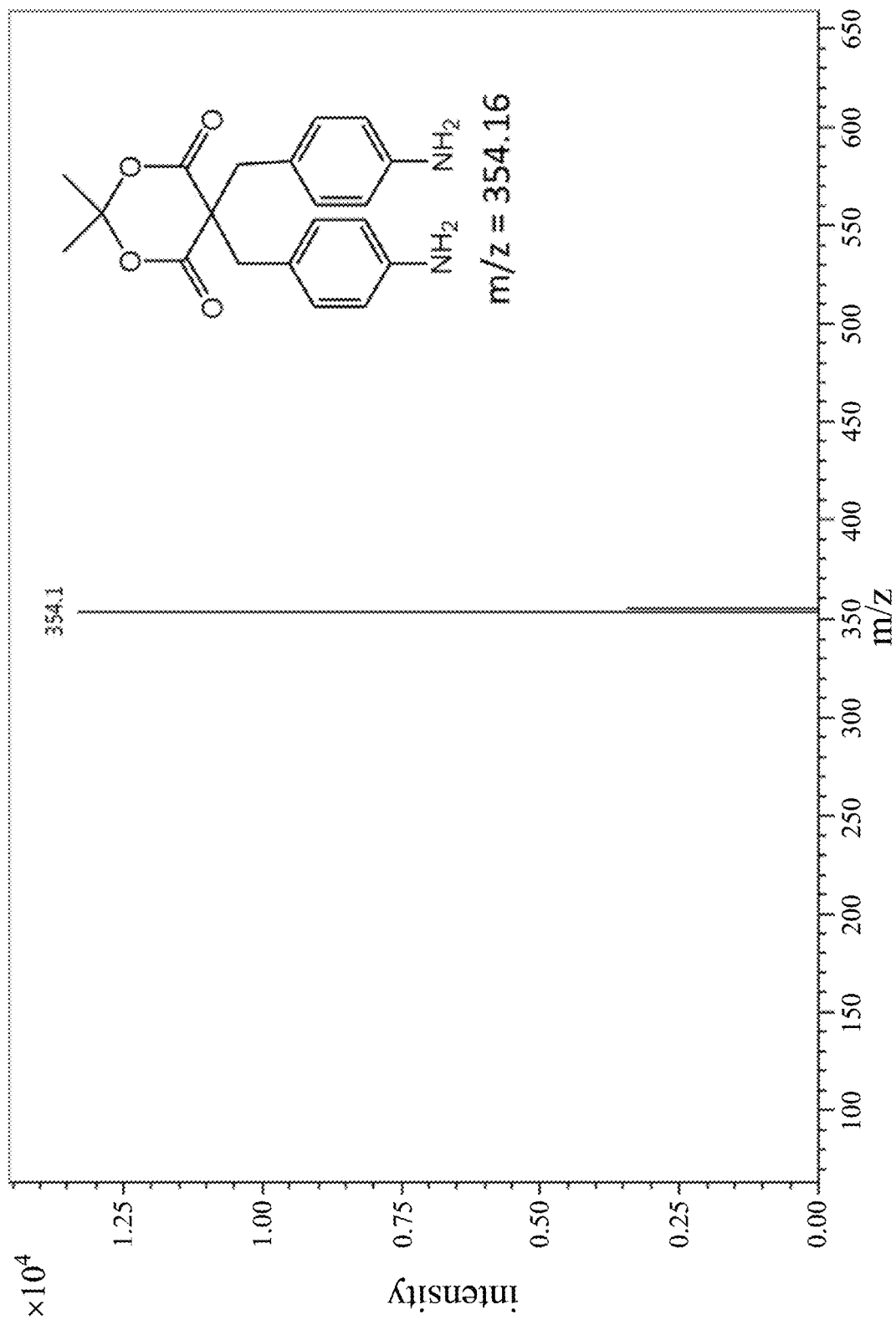
FIG. 3D is a mass spectrum of Example 1.

Example 1 is performed FTIR analysis, $^1$H-NMR analysis, $^{13}$C-NMR analysis, a mass spectrometry and an elemental analysis, so as to confirm the structure of Example 1. Please refer to FIGS. 3A, 3B, 3C and 3D. FIG. 3A is a FTIR spectrum of Synthesis Example 1 and Example 1. FIG. 3B is a $^1$H-NMR spectrum of Example 1. FIG. 3C is a $^{13}$C-NMR spectrum of Example 1. FIG. 3D is a mass spectrum of Example 1. The result of the elemental analysis is shown in Table 6, wherein the analytical value 1 and the analytical value 2 are represented the results of the elemental analysis tested twice. As known in FIGS. 3A to 3D, the product of Example 1 is the diamine compound (I-AA), and m/z is 354.16.

TABLE 6

|  | C(%) | H(%) | N(%) |
|---|---|---|---|
| analytical value 1 | 67.58 | 6.250 | 7.78 |
| analytical value 2 | 67.47 | 6.228 | 7.74 |
| theoretical value | 67.78 | 6.260 | 7.90 |

Example 2 of the present disclosure is a thermosetting resin obtained by the self-thermal crosslinking of Example 1. The synthesis method is to prepare the 25 wt % diamine compound (I-AA) solution in N-methyl-2-pyrrolidinone (NMP). Next, the solution is poured into a polydimethyl siloxane (PDMS) mold, and heated to 160° C. by the vacuum oven for 5 hours, and then heated at 180° C., 200° C. and 240° C. for 1 hour, respectively, so as to obtain the thermosetting resin of Example 2.

Figure 4:
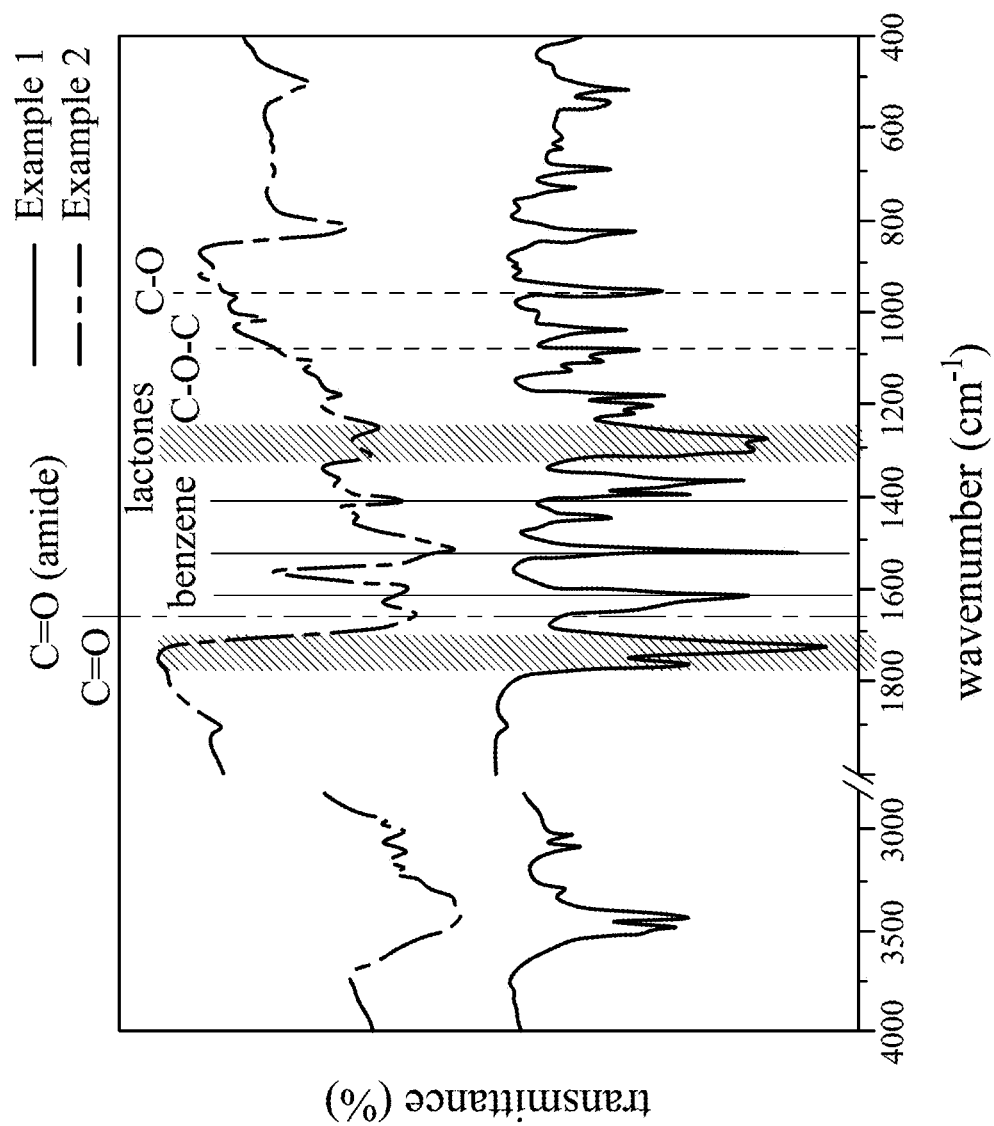
FIG. 4 is a FTIR spectrum of Example 1 and Example 2.

Example 2 is performed FTIR analysis to confirm the structure of Example 2. Please refer to FIG. 4, which is a FTIR spectrum of Example 1 and Example 2. As known in FIG. 4, Example 2 is the thermosetting resin obtained by the self-thermal crosslinking of Example 1.

Example 3 of the present disclosure is the polyimide (III). The synthesis method is to put 3 g (8.465 mmole) of the diamine compound (I-AA) and 35 mL of dry NMP in a 100 mL two-necked round-bottom flask. The inlet and outlet of the two-necked round-bottom flask is equipped with a condenser and nitrogen, respectively. The two-necked round-bottom flask is placed on a magnetic stirrer, and stirred at 25° C. until completely dissolved. Next, adding 3.76 g (8.465 mmole) of a dianhydride monomer (iv), and after reacting at the room temperature for 24 hours to form a polyamic acid (v). Afterward, adding 4.32 g (42.352 mmole) of acetic anhydride (AcO$_2$) and 3.348 g (43.325 mmole) of pyridine to perform the imidization reaction. The above solution is stirred for 2 hours at the room temperature, and then heated in an oil bath at 100° C. for 5 hours under nitrogen atmosphere. After cooling, the above solution is poured into 1L of methanol with constant stirring to produce a precipitate, and the precipitate is collected by the filtration and dried under vacuum to obtain the polyimide (III).

Figure 5A:
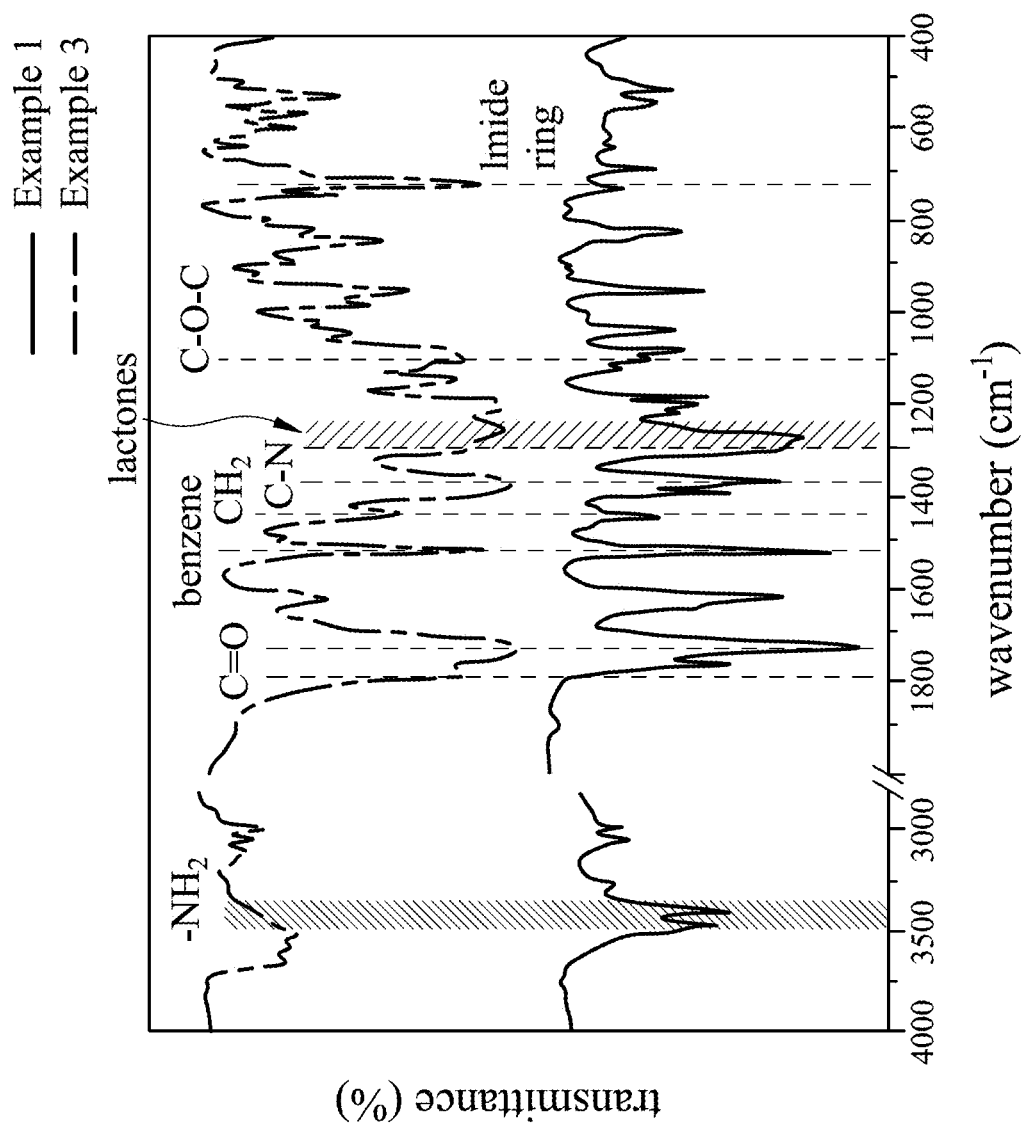
FIG. 5A is a FTIR spectrum of Example 1 and Example 3.
Figure 5B:
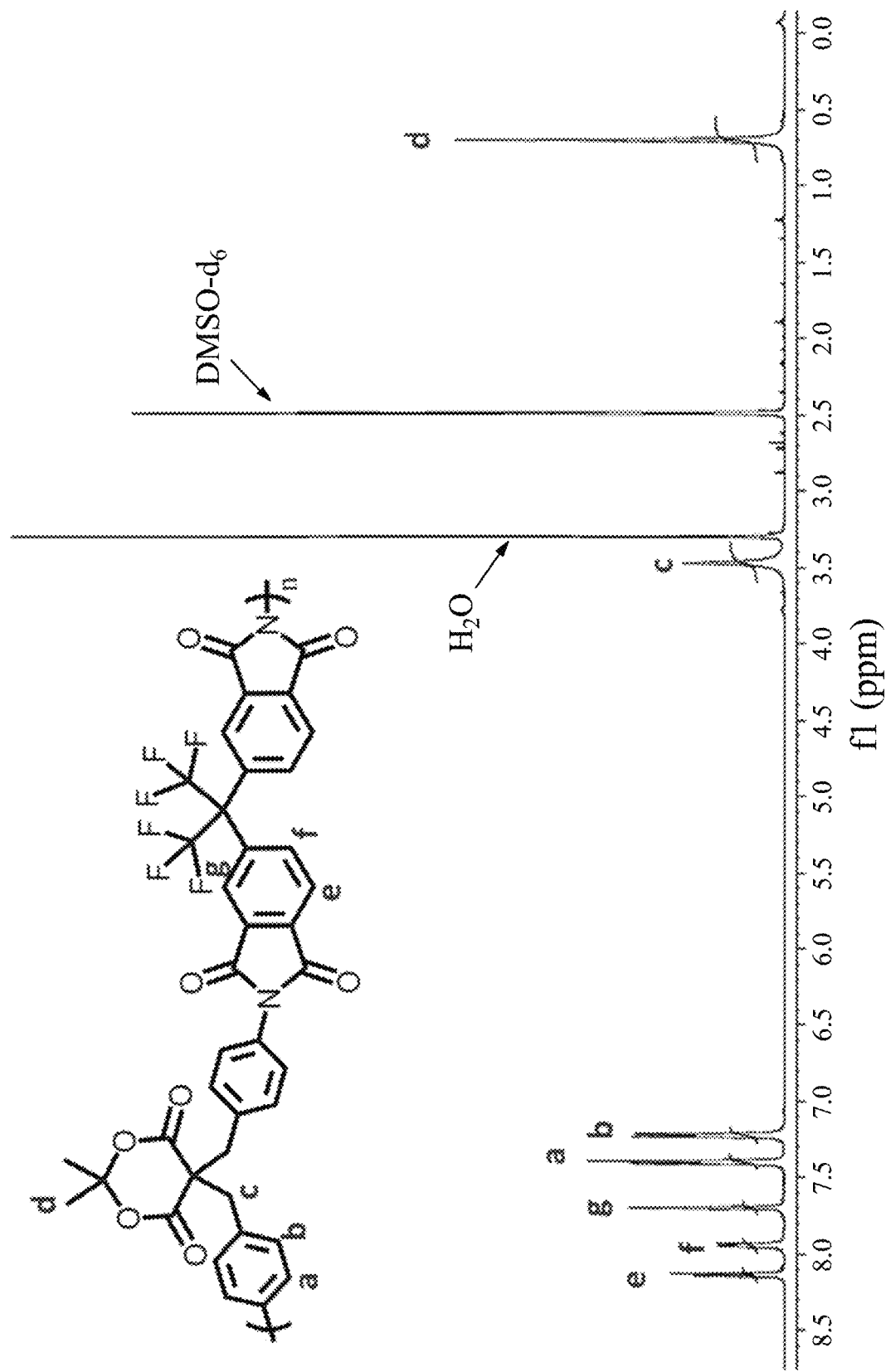
FIG. 5B is a $^1$H-NMR spectrum of Example 3.
Figure 5C:
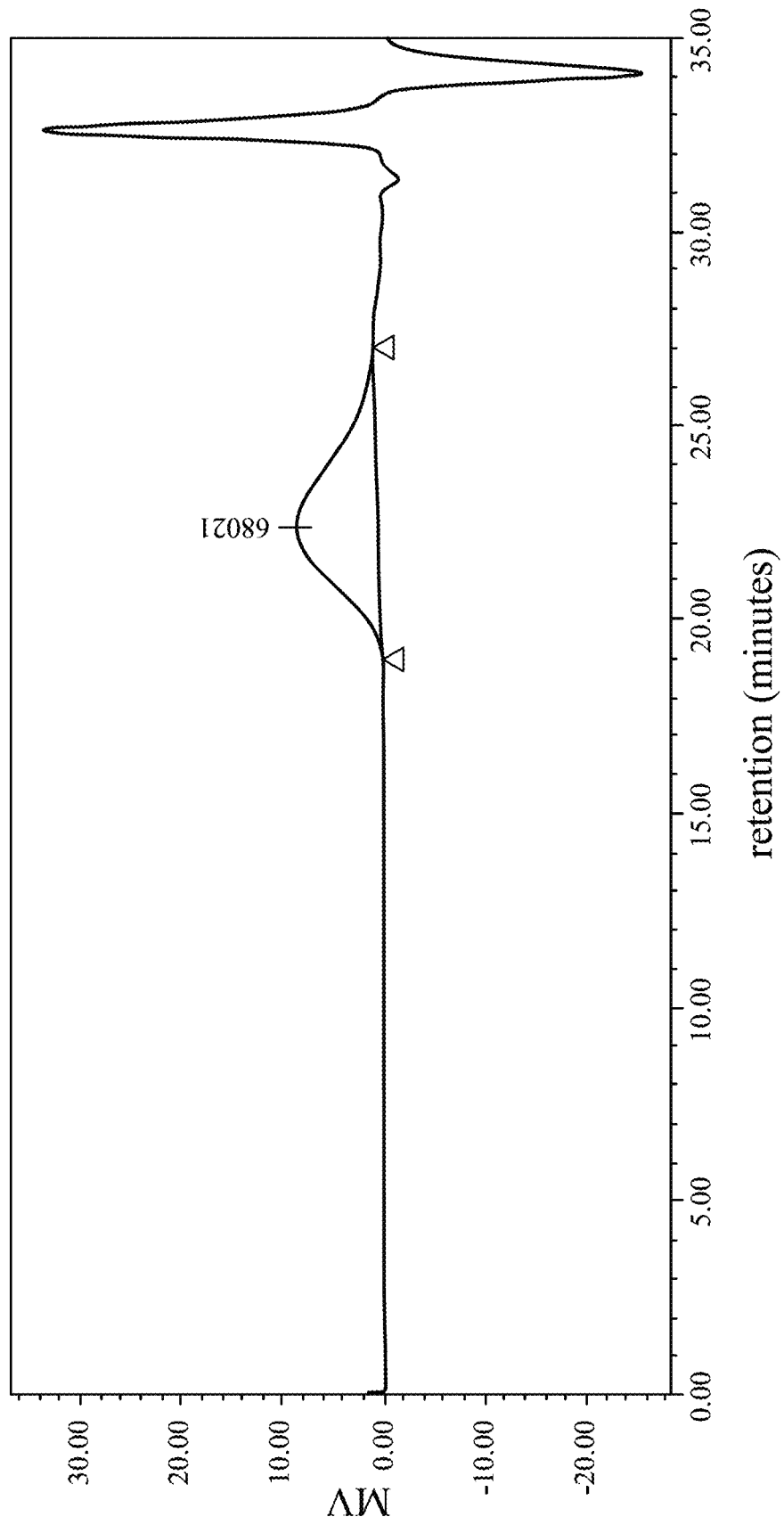
FIG. 5C is a GPC spectrum of Example 3.

Example 3 is performed FTIR analysis, $^1$H-NMR analysis and GPC analysis, so as to confirm the structure of Example 3. Please refer to FIGS. 5A, 5B and 5C. FIG. 5A is a FTIR spectrum of Example 1 and Example 3. FIG. 5B is a $^1$H-NMR spectrum of Example 3. FIG. 5C is a GPC spectrum of Example 3. As known in FIG. 5A and FIG. 5B, the product of Example 3 is the polyimide (III). From the analysis of FIG. 5C, the number average molecular weight ($M_{n,\ GPC}$), the weight average molecular weight ($M_{w,\ GPC}$), the peak molecular weight ($M_{p,\ GPC}$), Z average molecular weight ($M_{z,\ GPC}$), Z+1 average molecular weight ($M_{z+1,\ GPC}$) and the polydispersity index (PDI) are known. The measured results are shown in Table 7.

TABLE 7

| $M_n$ | $M_w$ | $M_p$ | $M_z$ | $M_{z+1}$ | PDI |
|---|---|---|---|---|---|
| 43062 | 77934 | 68021 | 122310 | 166884 | 1.81 |

Example 4 of the present disclosure is a product obtained by heating Example 3. The synthesis method is to prepare the 15 wt % of polyimide (III) solution in NMP solvent. Next, the solution is casted on the glass plate by 300 μm scraper, and heated to 100° C. by the vacuum oven for 24 hours, then heated at 150° C., 180° C., 200° C. and 250° C. for 1 hour, respectively, so as to obtain the polyimide (III) thin film of Example 4. Example 4 of the present disclosure is taken out at 250° C., and is represented by Example 4_250.

Figure 6:
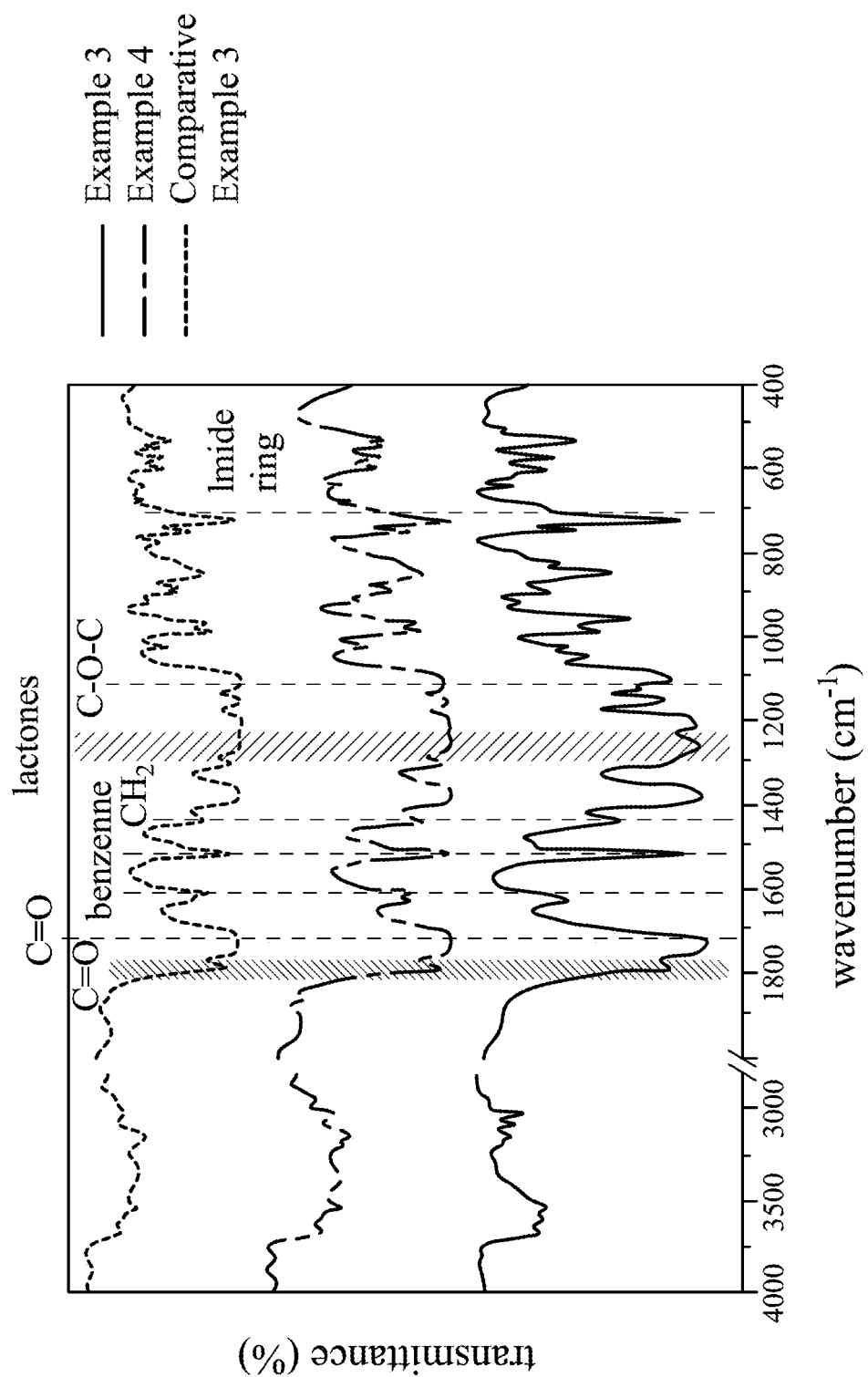
FIG. 6 is a FTIR spectrum of Example 3, Example 4 and Comparative Example 3.

Example 4 is performed FTIR analysis to confirm the structure of Example 4. Please refer to FIG. 6, which is a FTIR spectrum of Example 3, Example 4 and Comparative Example 3. The above Comparative Example 3 is a heated polyamic acid (v). As known in FIG. 6, after heating Example 3, Meldrum's acid on the segment can be functionalized and modified to obtain Example 4.

Example 5 of the present disclosure is the polybenzoxazine (IV). The synthesis method is to add 1 g (2.824 mmole) of the diamine compound (I-AA), 0.6646 g (2.824 mmole) of the diphenol monomer (B) and 0.3391 g (11.29 mmole) of the polyoxymethylene to a mixed solution of 3 mL of toluene and 1.5 mL of ethanol. The above solution is reacted at 80° C. for 72 hours, and 200 mL of methanol is added to the solution drop by drop to precipitate, the precipitate is collected by the filtration, and then heated at 40° C. by the vacuum oven for 24 hours to remove methanol, so as to obtain the polybenzoxazine (IV).

Figure 7A:
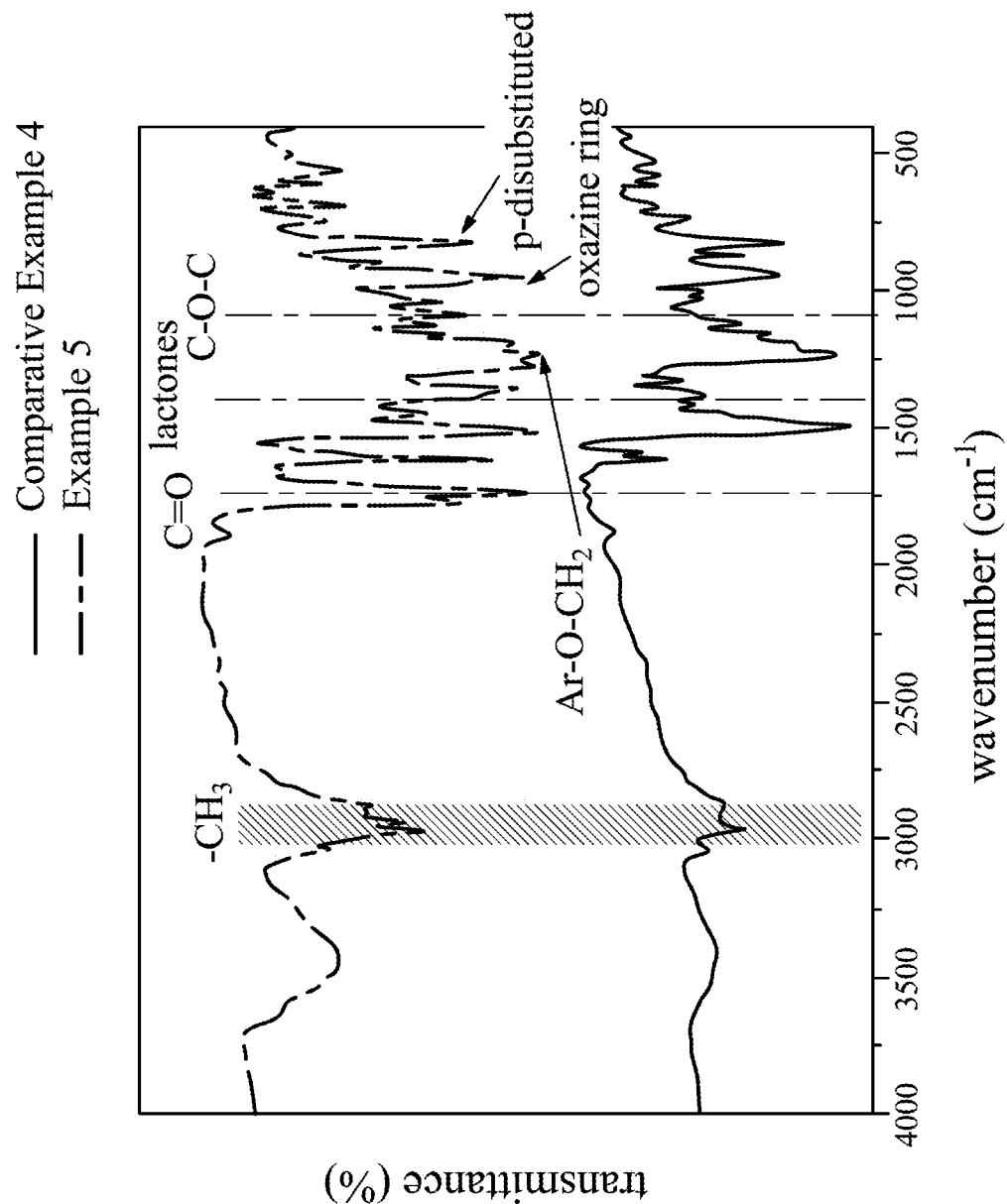
FIG. 7A is a FTIR spectrum of Example 5 and Comparative Example 4.
Figure 7B:
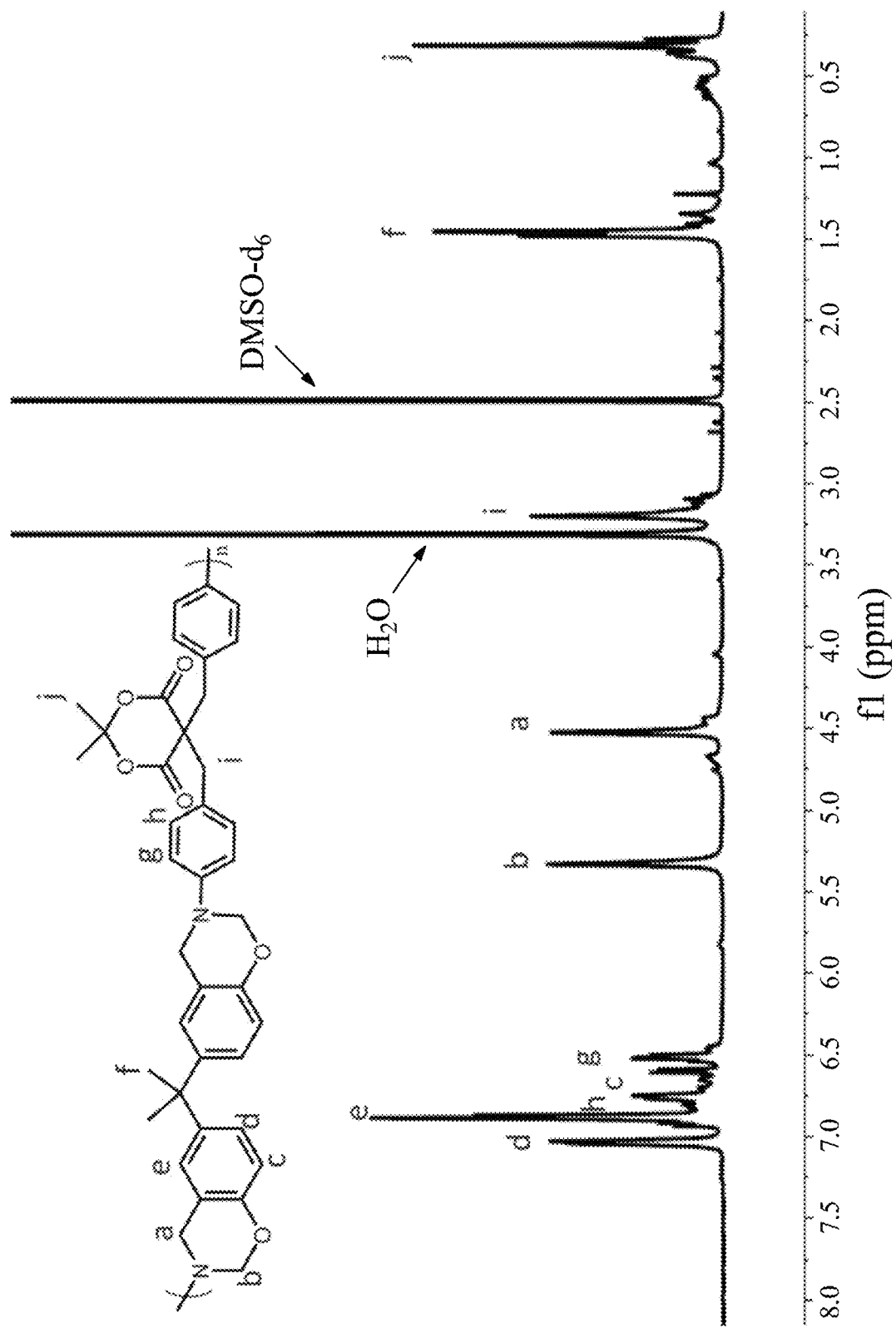
FIG. 7B is a $^1$H-NMR spectrum of Example 5.
Figure 7C:
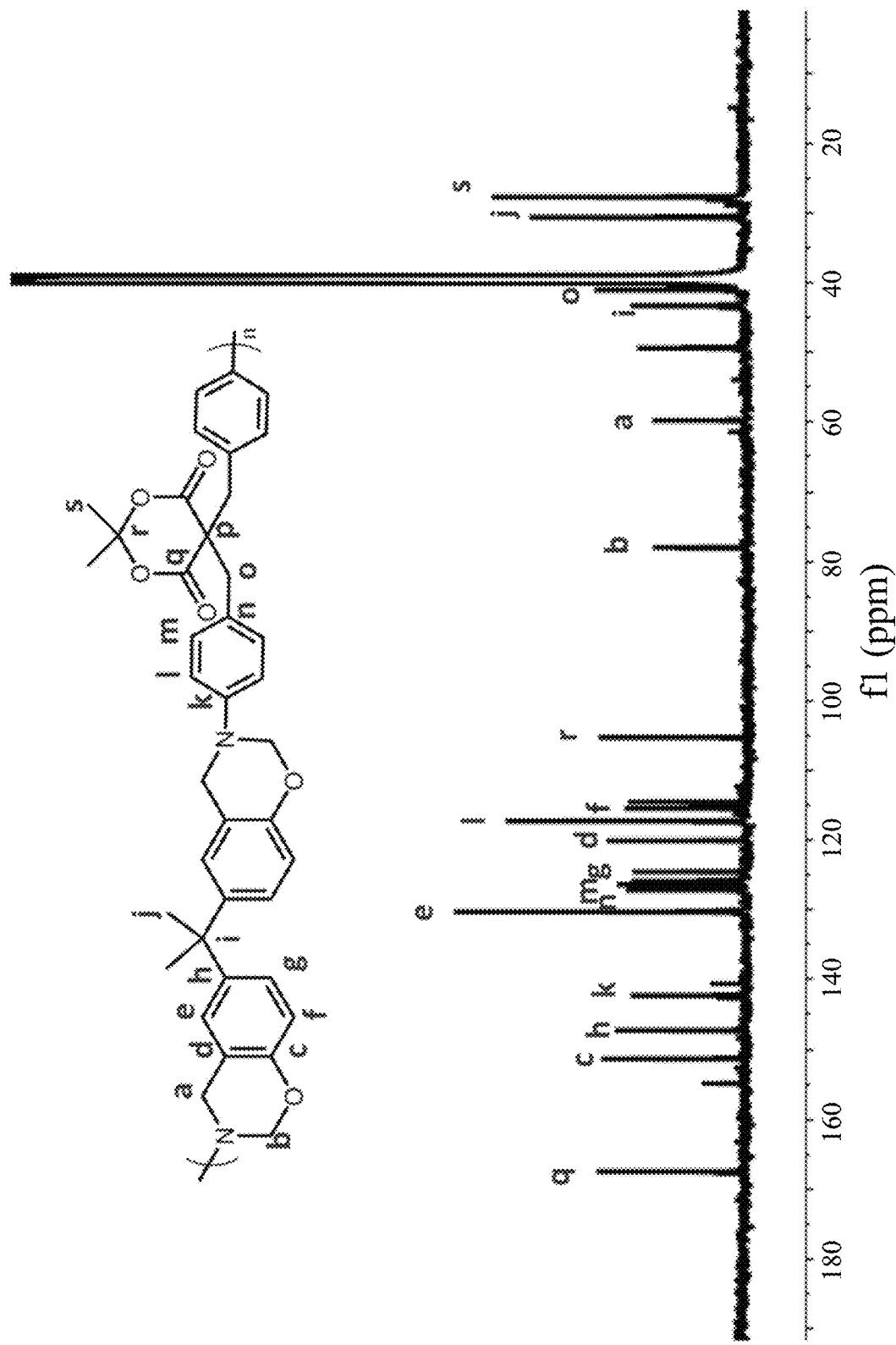
FIG. 7C is a $^{13}$C-NMR spectrum of Example 5.

Example 5 is performed FTIR analysis, $^1$H-NMR analysis and $^{13}$C-NMR analysis, so as to confirm the structure of Example 5. Please refer to FIGS. 7A, 7B and 7C. FIG. 7A is a FTIR spectrum of Example 5 and Comparative Example 4. FIG. 7B is a $^1$H-NMR spectrum of Example 5. FIG. 7C is a $^{13}$C-NMR spectrum of Example 5. Comparative Example 4 is a polybenzoxazine polymer (PBz-oda) prepared by using 4,4'-diaminodiphenyl ether, bisphenol A and polyoxymethylene. As known in FIGS. 7A to 7C, the product of Example 5 is the polybenzoxazine (IV).

Example 6 of the present disclosure is a product obtained by heating Example 5. The synthesis method is to prepare the 35 wt % of polybenzoxazine (IV) solution in NMP solvent. Next, the solution is casted on the glass plate by 100 μm scraper, and heated to 80° C. by the vacuum oven for one night, then heated at 150° C., 180° C., 200° C. and 240° C. for 1 hour, respectively, so as to obtain the polybenzoxazine (IV) thin film of Example 6. Example 6 of the present disclosure is taken out at 240° C., and is represented by Example 6_240.

Figure 8:
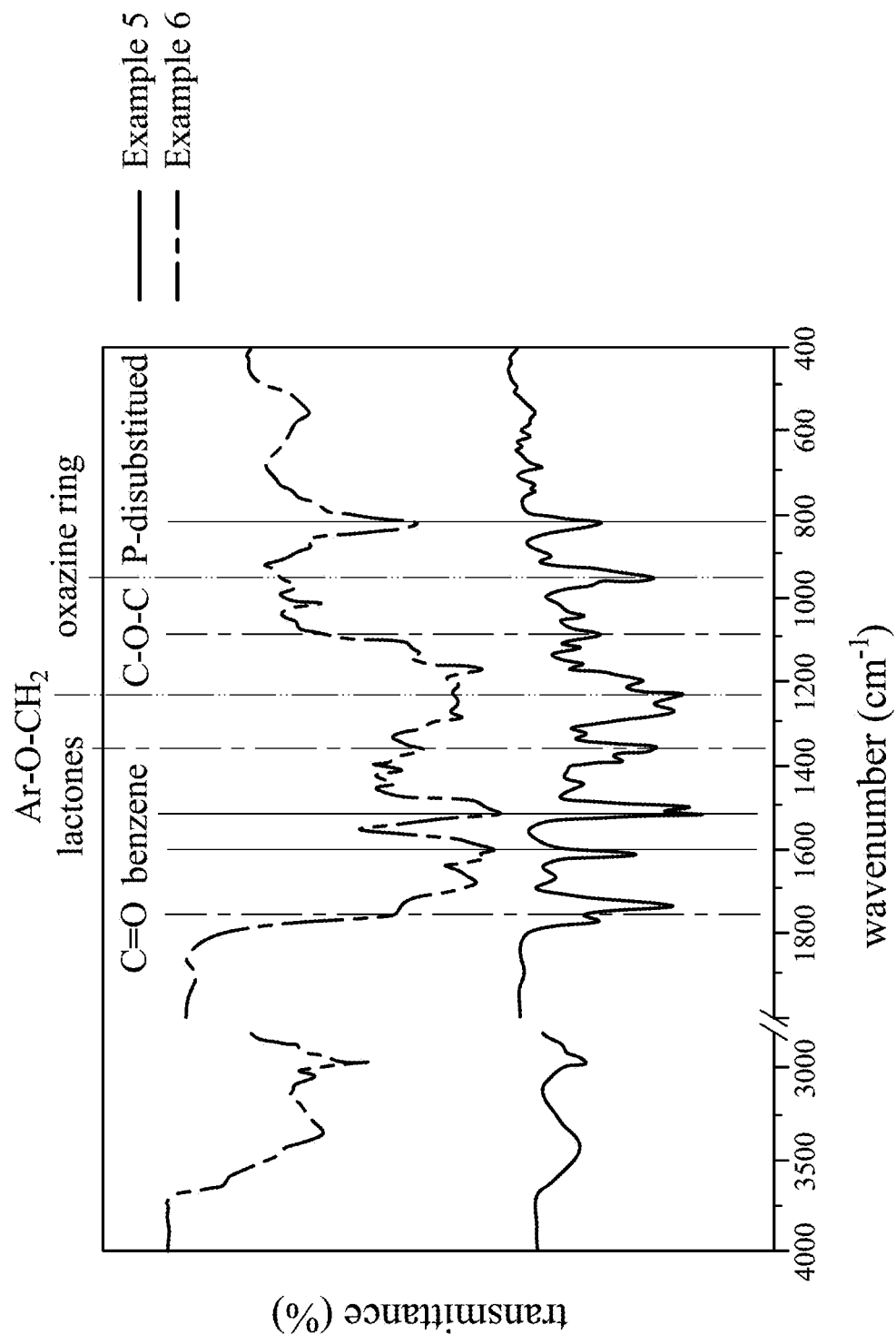
FIG. 8 is a FTIR spectrum of Example 5 and Example 6.

Example 6 is performed FTIR analysis to confirm the structure of Example 6. Please refer to FIG. 8, which is a FTIR spectrum of Example 5 and Example 6. As known in FIG. 8, after heating Example 5, Meldrum's acid on the segment can be functionalized and modified to obtain Example 6.

Example 7 of the present disclosure is the polyamide polymer material (II) prepared by a ring-opening self-polymerization of Example 1. The synthesis method is to prepare the 30 wt % of diamine compound (I-AA) solution in NMP solvent. The solution is reacted in an oil bath at 180° C. for 6 hours, and then precipitated in the aqueous methanol solution to obtain the polyamide polymer material (II). Furthermore, Example 8 is a product obtained by heating Example 7. The synthesis method is to prepare the 15 wt % of polyamide polymer material (II) solution in NMP solvent. Next, the solution is casted on the glass plate by 200 μm scraper, and heated to 120° C. by the vacuum oven for 24 hours, then heated at 180° C. and 200° C. for 2 hour, respectively, further heated at 240° C. for 1 hour, so as to obtain the polyamide polymer material (II) thin film of Example 8. Example 8 prepared by the above respective heating temperatures can be represented by Example 8_180, Example 8_200 and Example 8_240.

Figure 9A:
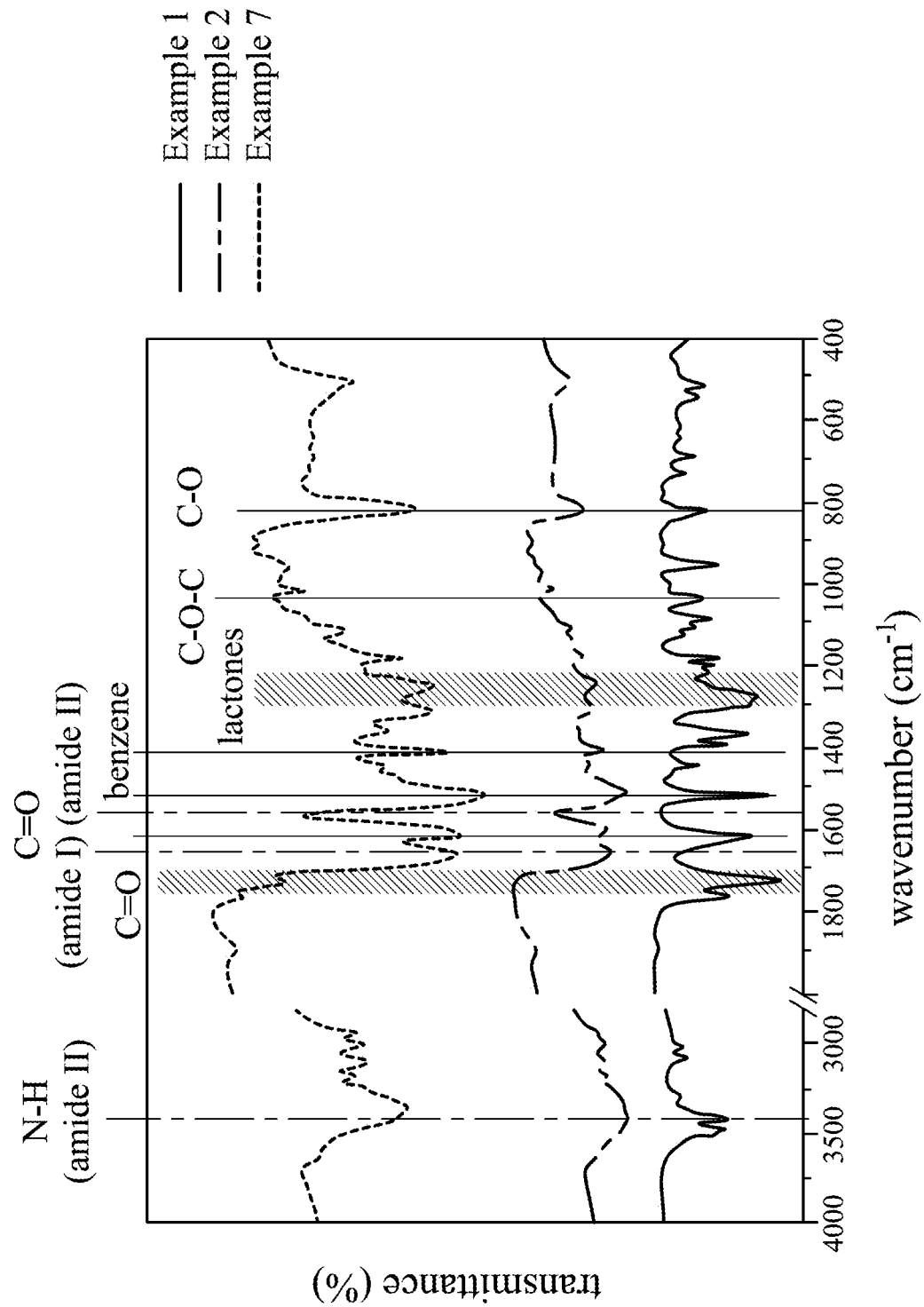
FIG. 9A is a FTIR spectrum of Example 1, Example 2 and Example 7.
Figure 9B:
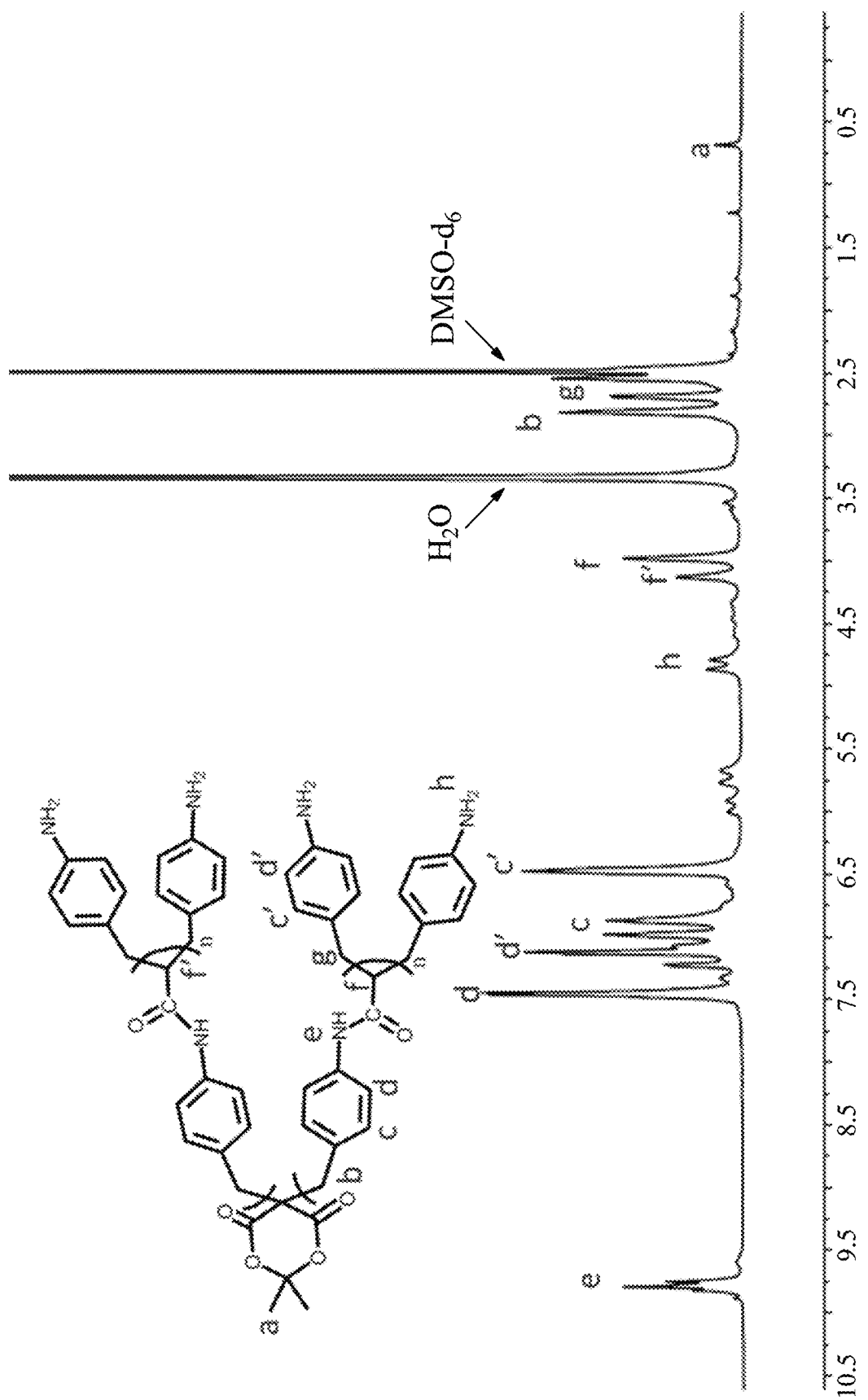
FIG. 9B is a $^1$H-NMR spectrum of Example 7.

Example 7 is performed FTIR analysis and $^1$H-NMR analysis, so as to confirm the structure of Example 7. Please refer to FIGS. 9A and 9B. FIG. 9A is a FTIR spectrum of Example 1, Example 2 and Example 7. FIG. 9B is a $^1$H-NMR spectrum of Example 7. As known in FIGS. 9A and 9B, Example 7 is the polyamide polymer material (II) prepared by the ring-opening self-polymerization of Example 1.

Thermal Property Measurement

Synthesis Example 1, Example 1 to Example 7, and Comparative Example 1 to Comparative Example 5 are performed the thermal property evaluation. The thermal property evaluation methods include differential scanning calorimetry (DSC), thermogravimetric analysis (TGA) and dynamic mechanical analysis (DMA).

Figure 10A:
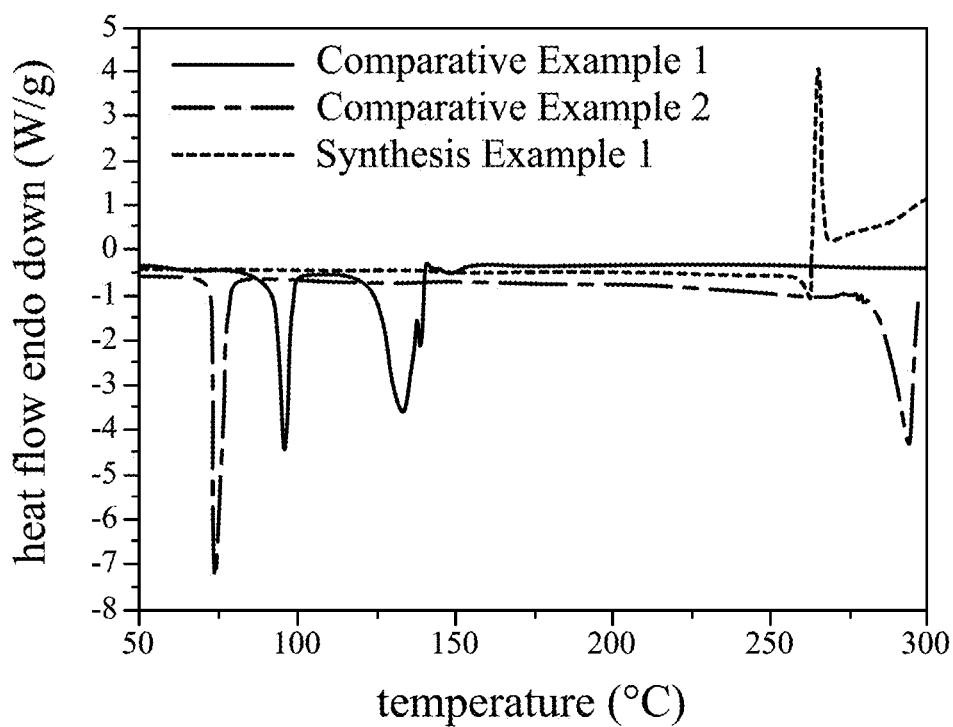
FIG. 10A is a DSC thermogram of Comparative Example 1, Comparative Example 2 and Synthesis Example 1.
Figure 10B:
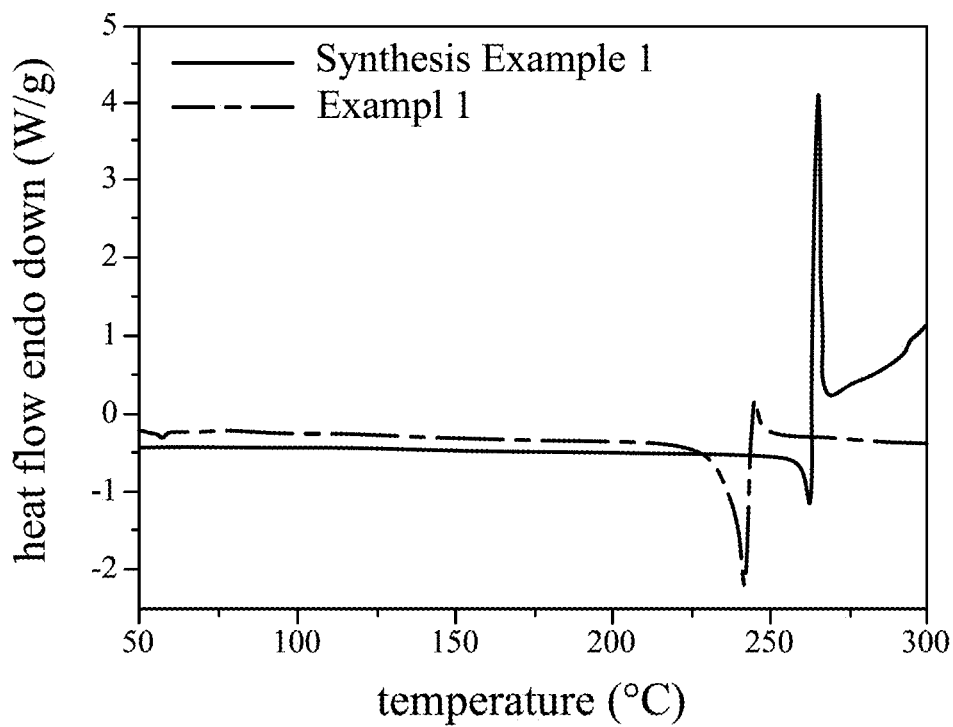
FIG. 10B is a DSC thermogram of Synthesis Example 1 and Example 1.
Figure 10C:
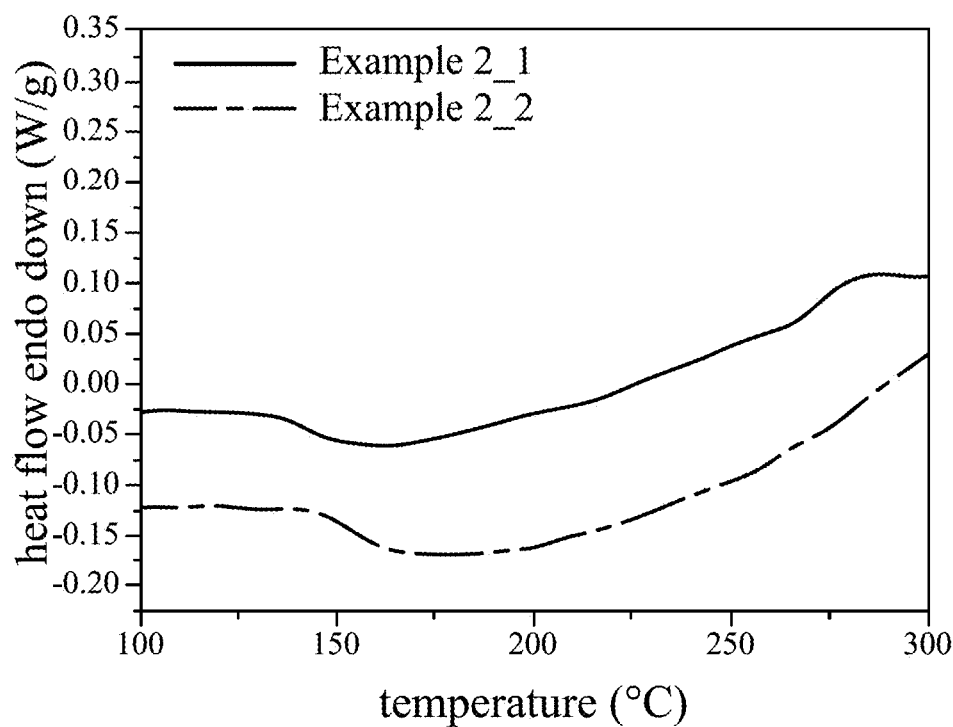
FIG. 10C is a DSC thermogram of Example 2 tested twice.
Figure 10D:
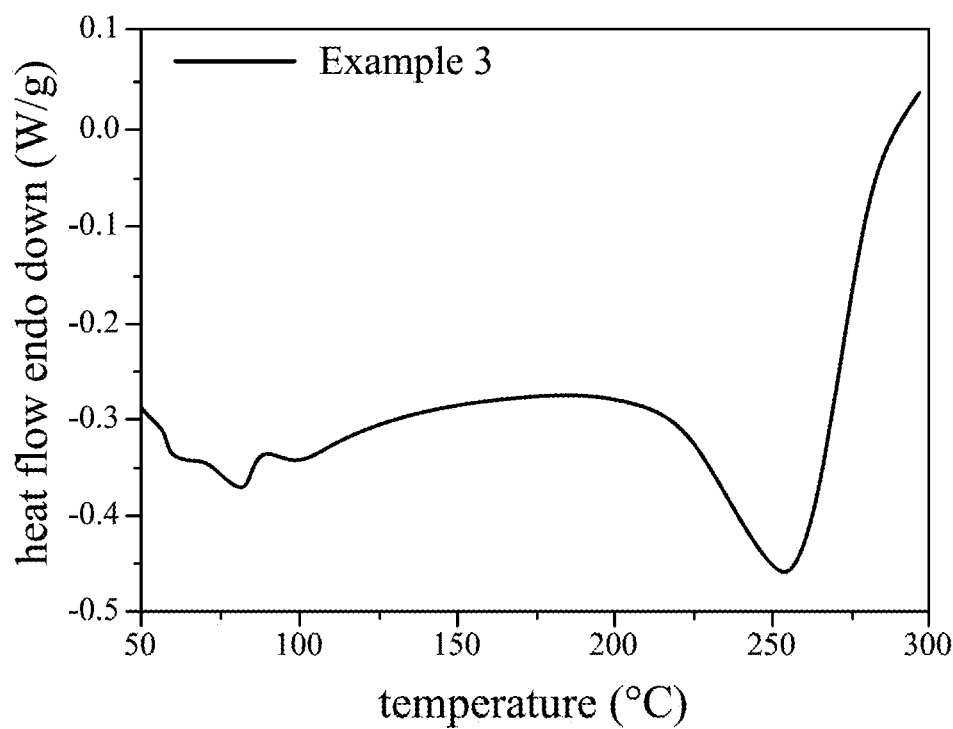
FIG. 10D is a DSC thermogram of Example 3.
Figure 10E:
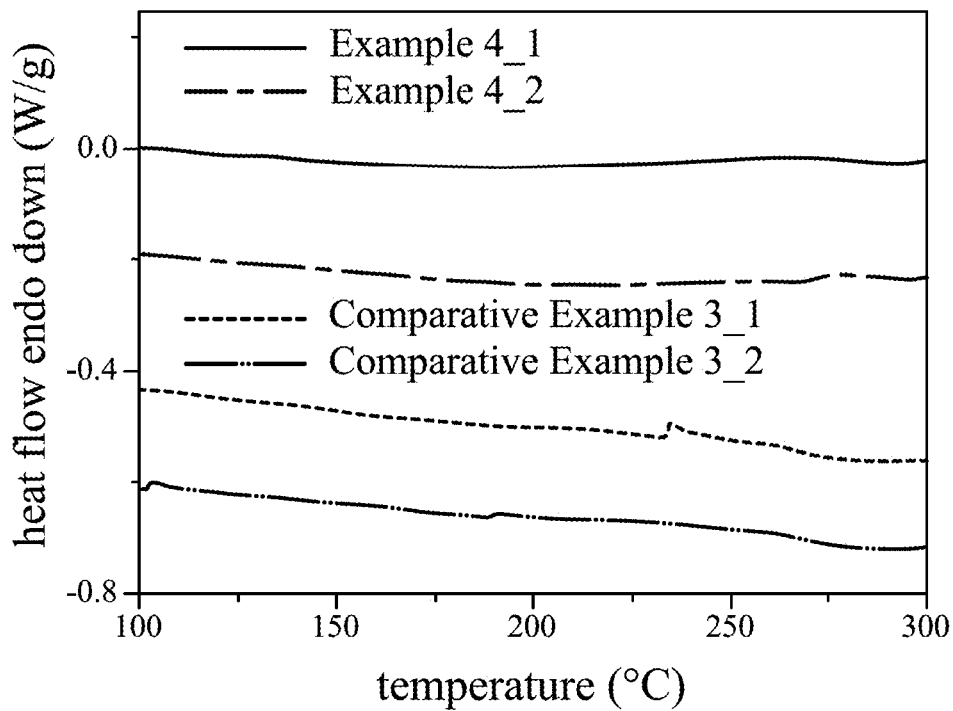
FIG. 10E is a DSC thermogram of each of Example 4 and Comparative Example 3 tested twice.
Figure 10F:
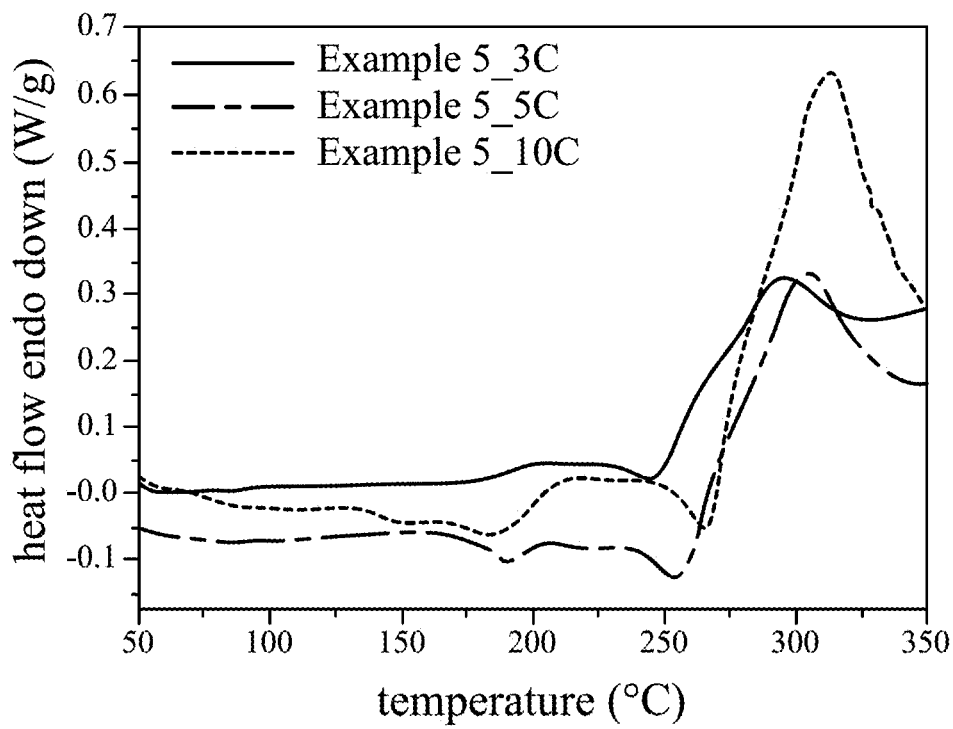
FIG. 10F is a DSC thermogram of Example 5.
Figure 10G:
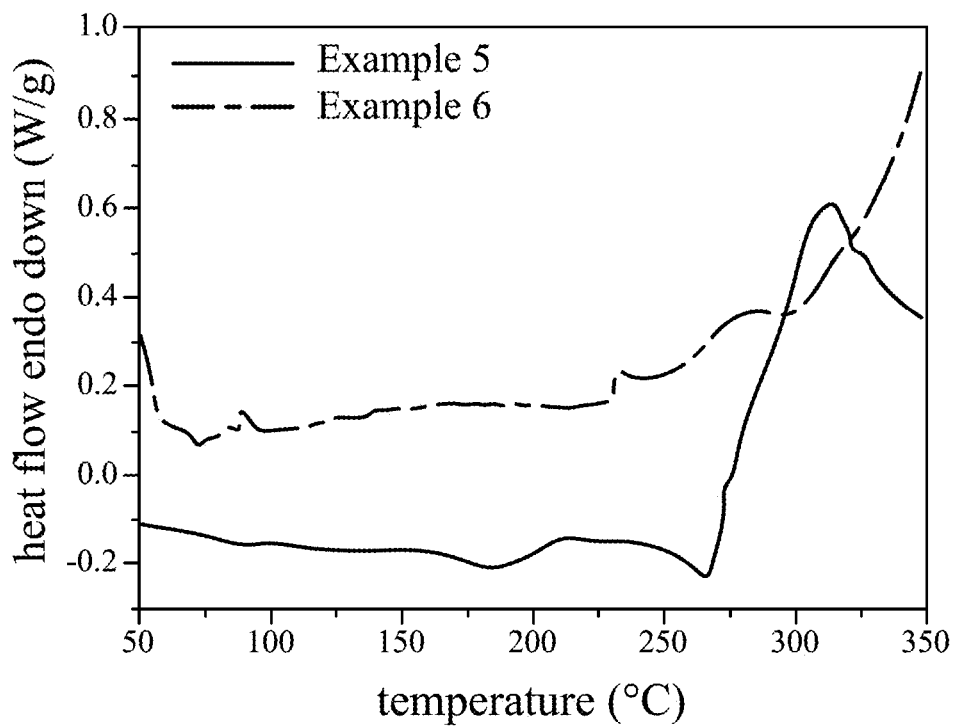
FIG. 10G is a DSC thermogram of Example 5 and Example 6.
Figure 10H:
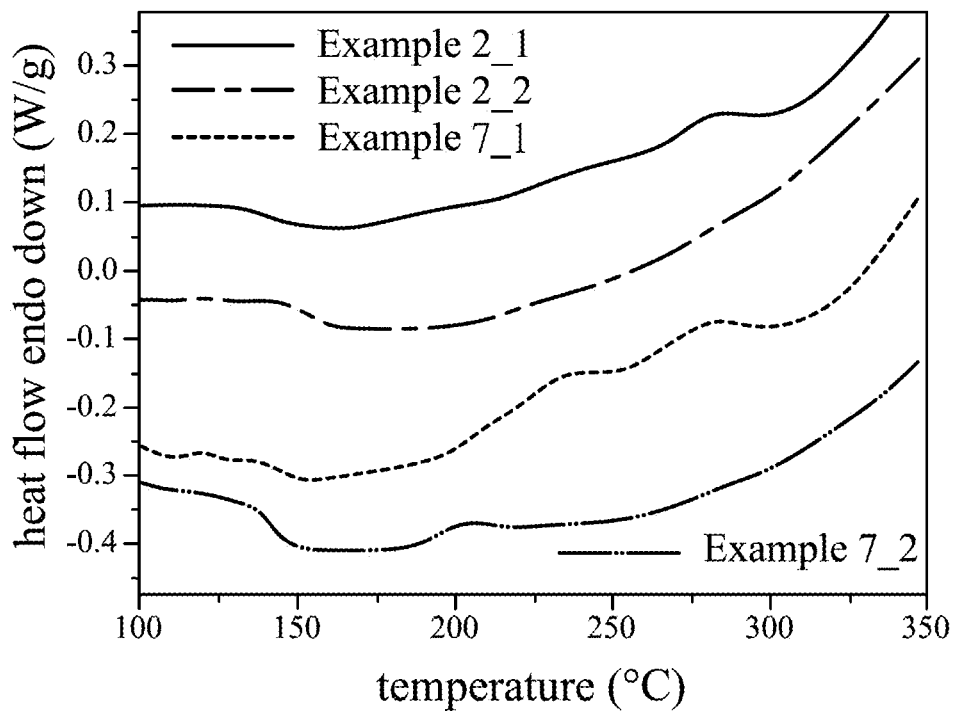
FIG. 10H is a DSC thermogram of each of Example 2 and Example 7 tested twice.

Please refer to FIGS. 10A, 10B, 10C, 10D, 10E, 10F, 10G and 10H. FIG. 10A is a DSC thermogram of Comparative Example 1, Comparative Example 2 and Synthesis Example 1. FIG. 10B is a DSC thermogram of Synthesis Example 1 and Example 1. FIG. 10C is a DSC thermogram of Example 2 tested twice. FIG. 10D is a DSC thermogram of Example 3. FIG. 10E is a DSC thermogram of each of Example 4 and Comparative Example 3 tested twice. FIG. 10F is a DSC thermogram of Example 5. FIG. 10G is a DSC thermogram of Example 5 and Example 6. FIG. 10H is a DSC thermogram of each of Example 2 and Example 7 tested twice. In FIG. 10F, Example 5_3C, Example 5_5C and Example 5_10C are the temperature rise rates measured by Example 5 in DSC, which are 3° C./min, 5° C./min and 10° C./min, respectively, so as to track the crosslinking reaction.

Figure 11A:
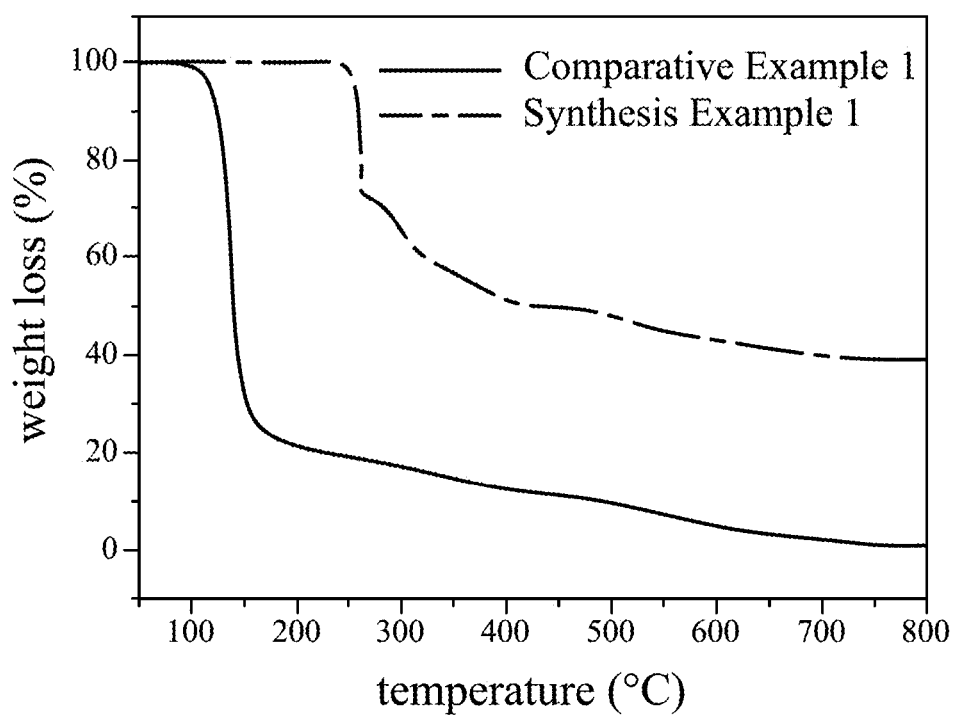
FIG. 11A is a TGA thermogram of Comparative Example 1 and Synthesis Example 1.
Figure 11B:
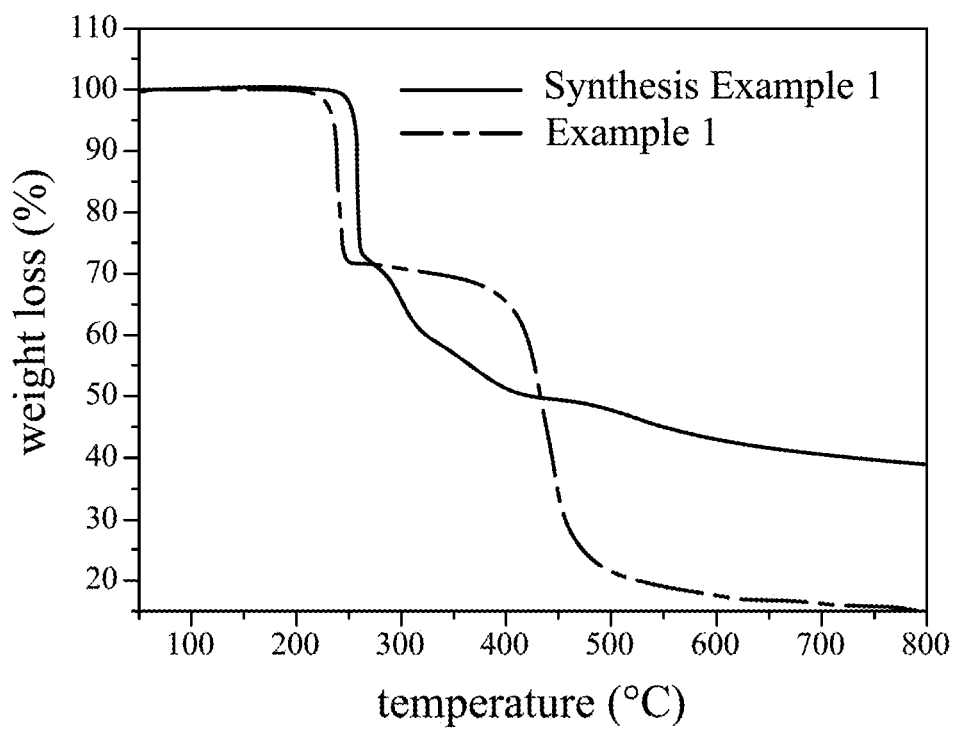
FIG. 11B is a TGA thermogram of Synthesis Example 1 and Example 1.
Figure 11C:
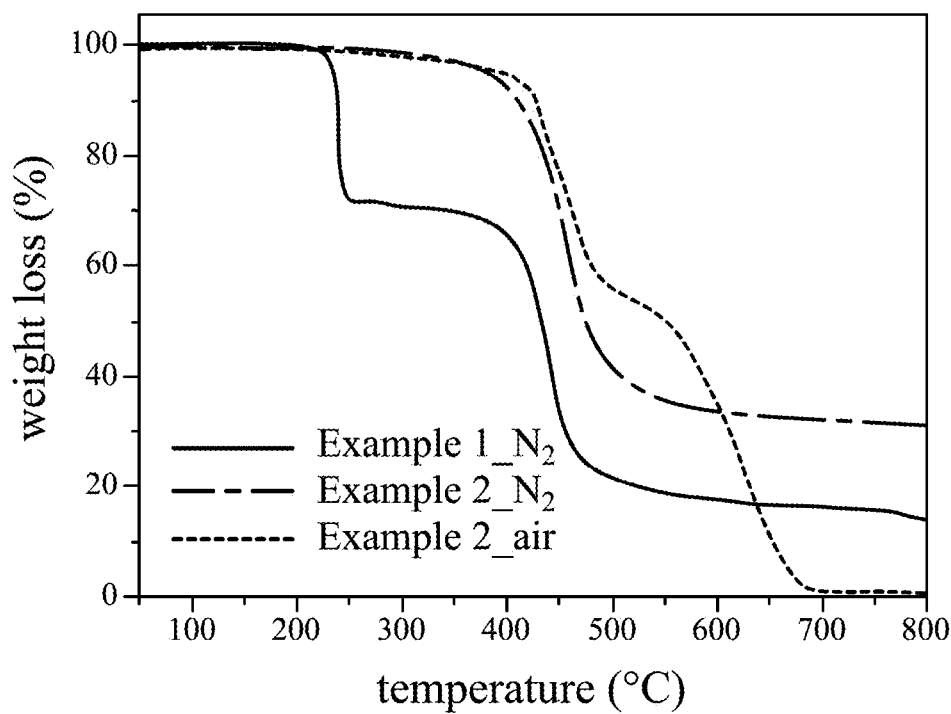
FIG. 11C is a TGA thermogram of Example 1 and Example 2 under air and nitrogen.
Figure 11D:
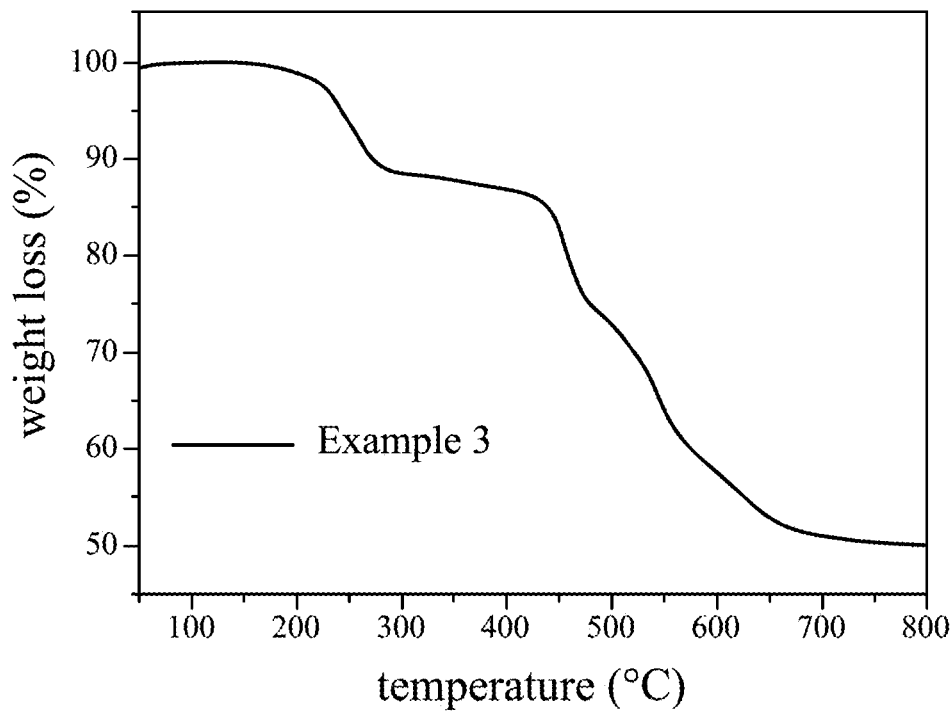
FIG. 11D is a TGA thermogram of Example 3.
Figure 11E:
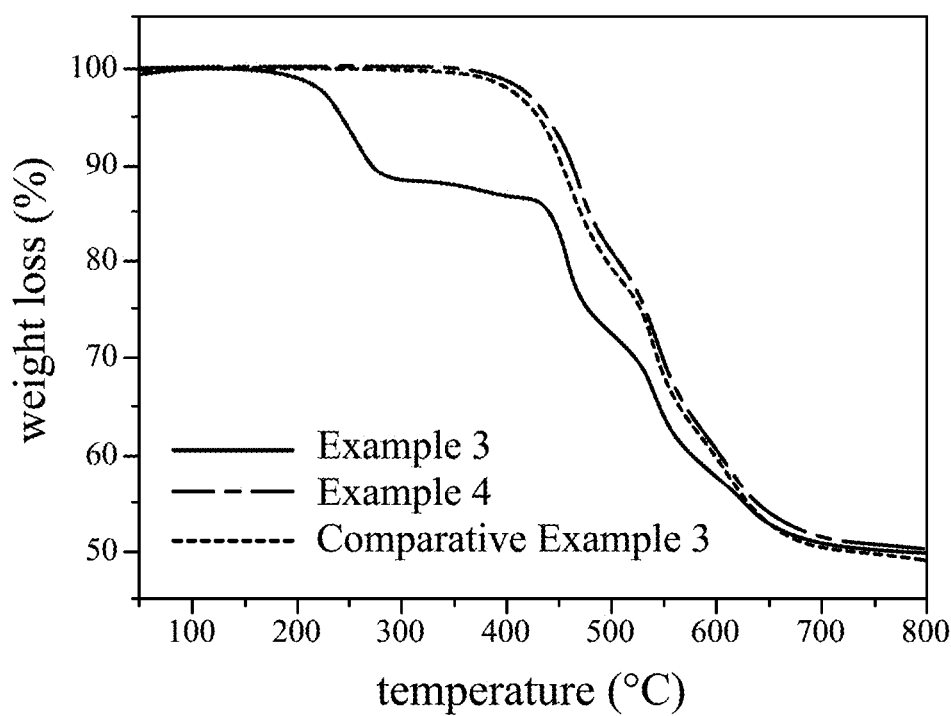
FIG. 11E is a TGA thermogram of Example 3, Example 4 and Comparative Example 3.
Figure 11F:
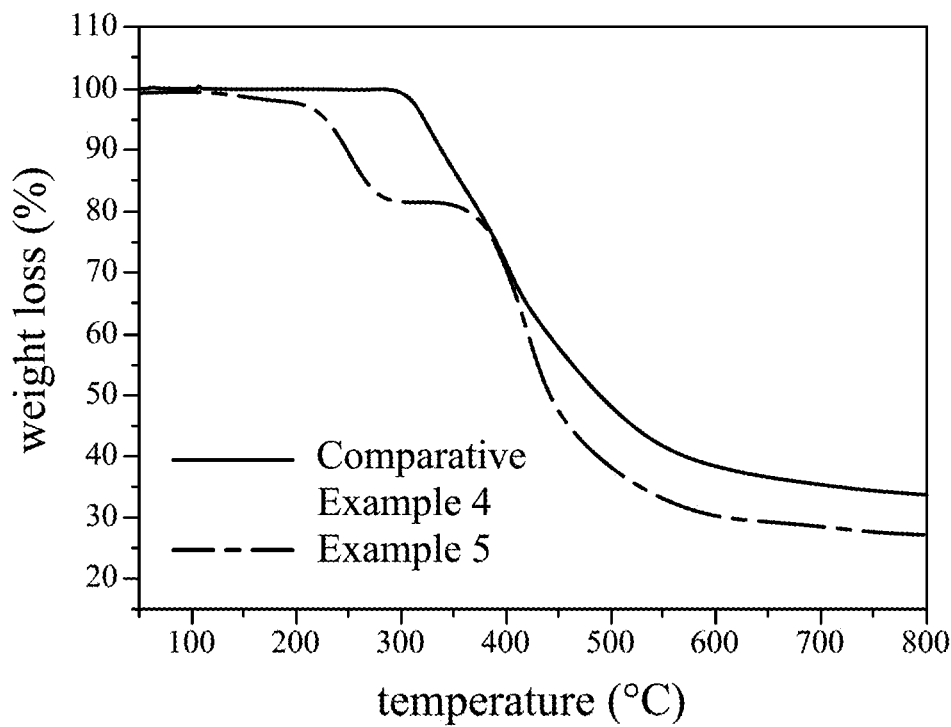
FIG. 11F is a TGA thermogram of Example 5 and Comparative Example 4.
Figure 11G:
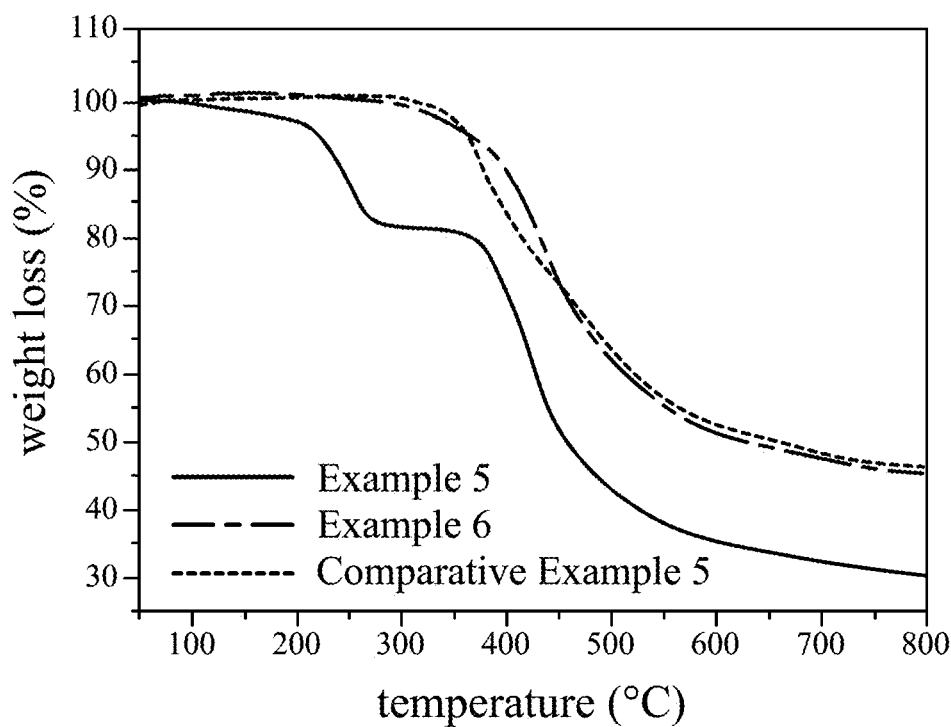
FIG. 11G is a TGA thermogram of Example 5, Example 6 and Comparative Example 5.
Figure 11H:
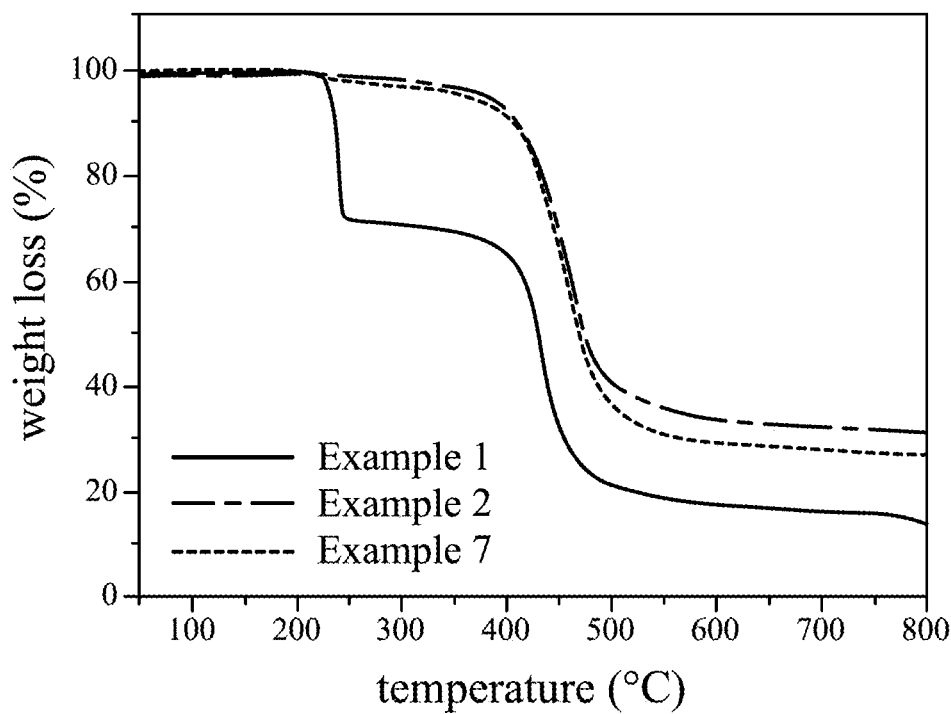
FIG. 11H is a TGA thermogram of Example 1, Example 2 and Example 7.

Please refer to FIGS. 11A, 11B, 11C, 11D, 11E, 11F, 11G and 11H. FIG. 11A is a TGA thermogram of Comparative Example 1 and Synthesis Example 1. FIG. 11B is a TGA thermogram of Synthesis Example 1 and Example 1. FIG. 11C is a TGA thermogram of Example 1 and Example 2 under air and nitrogen. FIG. 11D is a TGA thermogram of Example 3. FIG. 11E is a TGA thermogram of Example 3, Example 4 and Comparative Example 3. FIG. 11F is a TGA thermogram of Example 5 and Comparative Example 4. FIG. 11G is a TGA thermogram of Example 5, Example 6 and Comparative Example 5. FIG. 11H is a TGA thermogram of Example 1, Example 2 and Example 7. The above Comparative Example 5 is a heated polybenzoxazine polymer (PBz-oda).

The glass transition temperature (Tg) and the thermal cracking temperature (Td) of Synthesis Example 1, Example 1 to Example 7, and Comparative Example 1 to Comparative Example 5 are known by DSC analysis and TGA analysis. The measurement results are shown in Table 8.

TABLE 8

| | Tg (° C.) | Td (° C.) |
|---|---|---|
| Synthesis Example 1 | * | 260 |
| Example 1 | * | 250 |
| Example 2 | 141 | 420 |
| Example 3 | 235 | 240 |
| Example 4 | 256 | 430 |
| Example 5 | 175 | 225 |
| Example 6 | 258 | 400 |
| Example 7 | 145 | 420 |
| Comparative Example 1 | * | 148 |
| Comparative Example 2 | * | — |
| Comparative Example 3 | 302 | 400 |
| Comparative Example 4 | — | 348 |
| Comparative Example 5 | 267 | 350 |

Note:
"—" is represented as unmeasured.
"*" is represented as unable to measure.

Figure 12A:
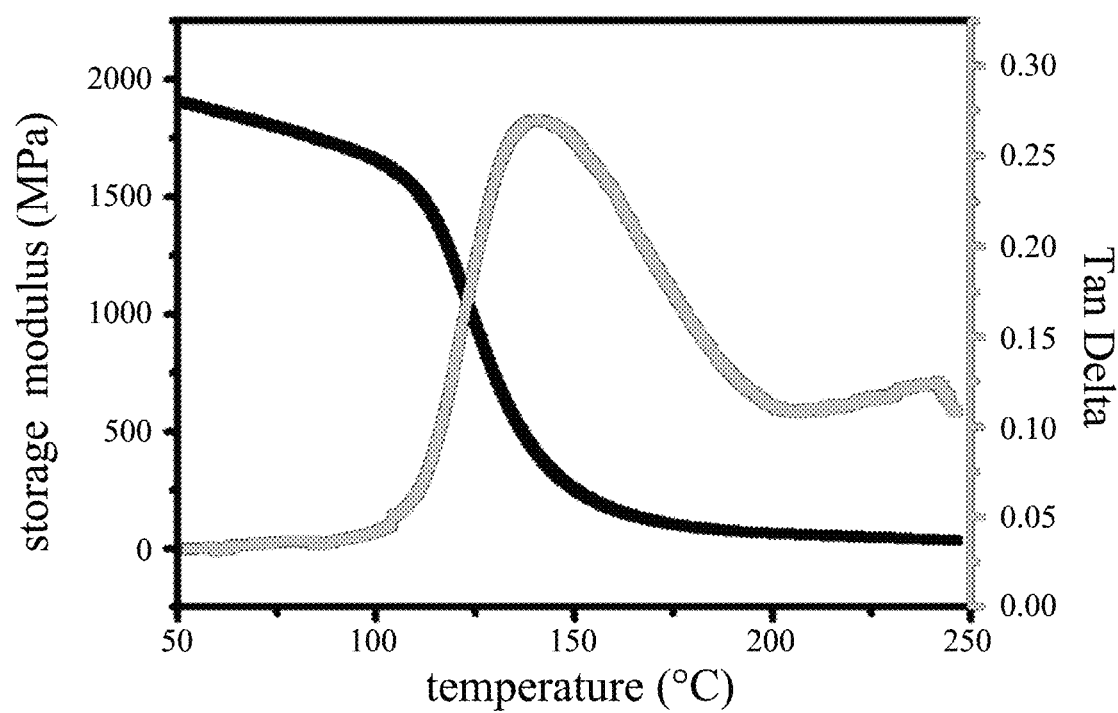
FIG. 12A is a DMA thermogram of Example 2.
Figure 12B:
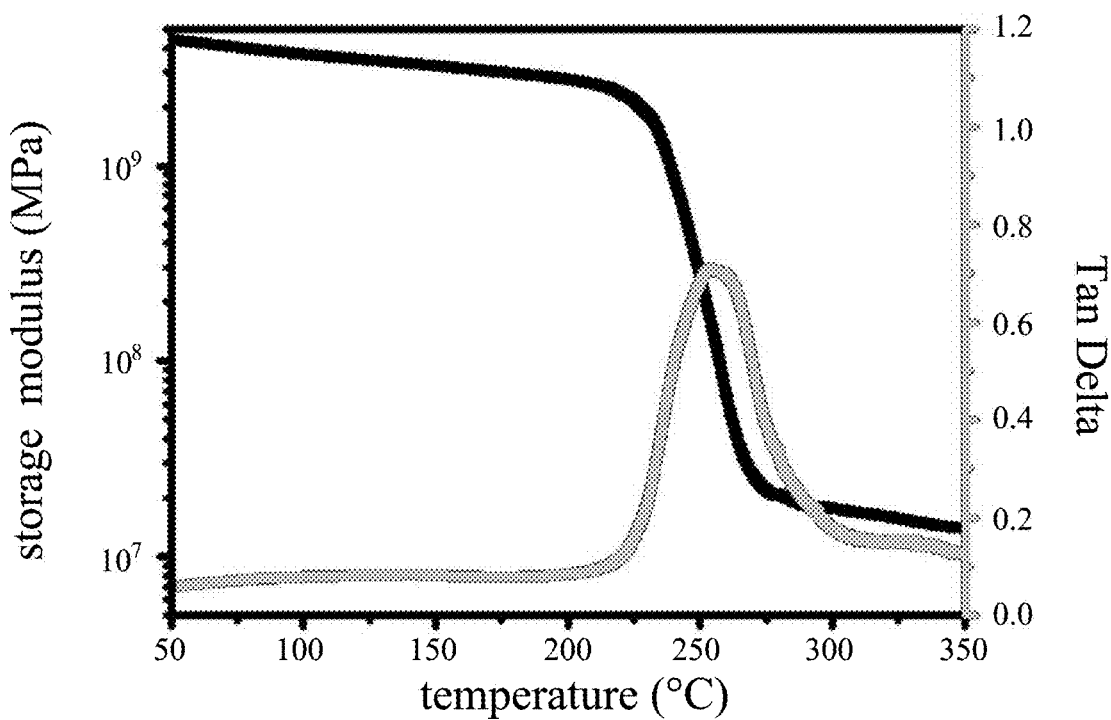
FIG. 12B is a DMA thermogram of Example 4_250.
Figure 12C:
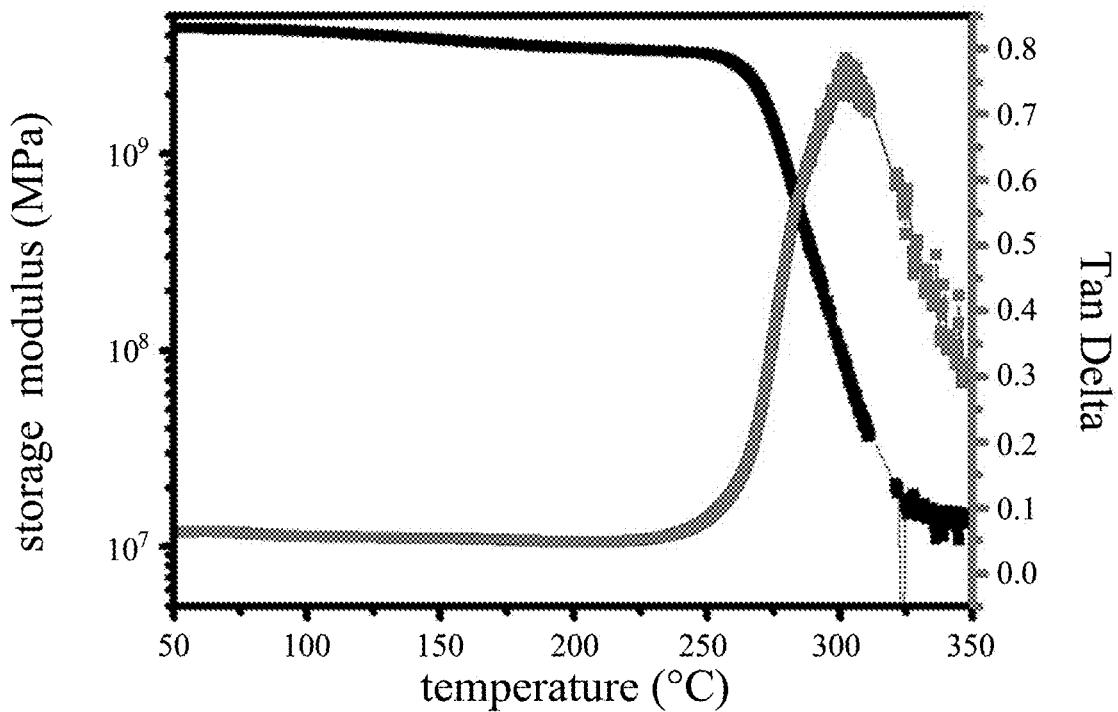
FIG. 12C is a DMA thermogram of Comparative Example 3.
Figure 12D:
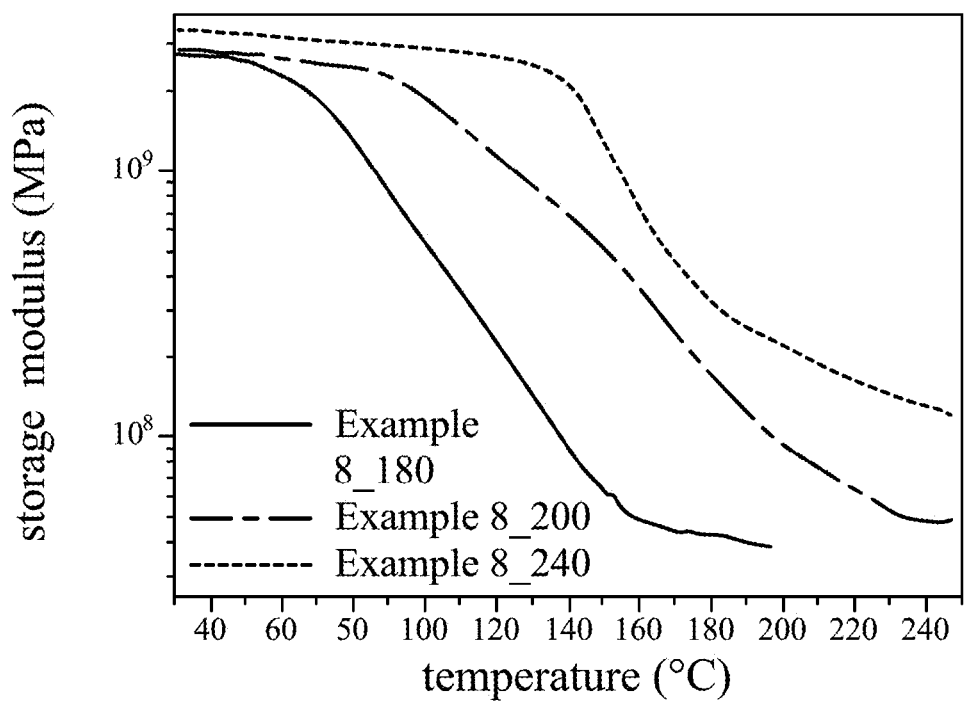
FIGS. 12D and 12E are DMA thermograms of Example 8_180, Example 8_200 and Example 8_240.
Figure 12E:
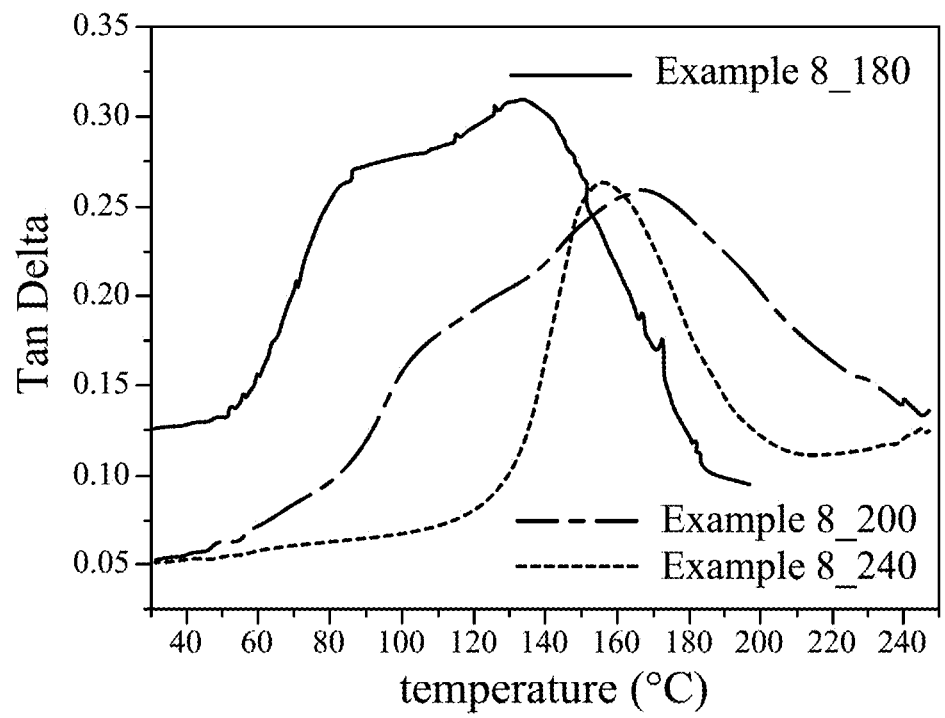

Please refer to FIGS. 12A, 12B, 12C, 12D and 12E. FIG. 12A is a DMA thermogram of Example 2. FIG. 12B is a DMA thermogram of Example 4_250. FIG. 12C is a DMA thermogram of Comparative Example 3. FIGS. 12D and 12E are DMA thermograms of Example 8_180, Example 8_200 and Example 8_240.

The glass transition temperature (Tg) and the storage modulus at 50° C. of Example 2, Example 4, Example 8 and Comparative Example 3 are known by DMA analysis. The measurement results are shown in Table 9.

TABLE 9

| | Tg (° C.) | storage modulus (MPa) |
|---|---|---|
| Example 2 | 141 | 1904 |
| Example 4_250 | 256 | 4380 |
| Comparative Example 3 | 302 | 4437 |
| Example 8_180 | 132 | 2588 |
| Example 8_200 | 168 | 2737 |
| Example 8_240 | 156 | 3257 |

Mechanical Property Measurement

Figure 13A:
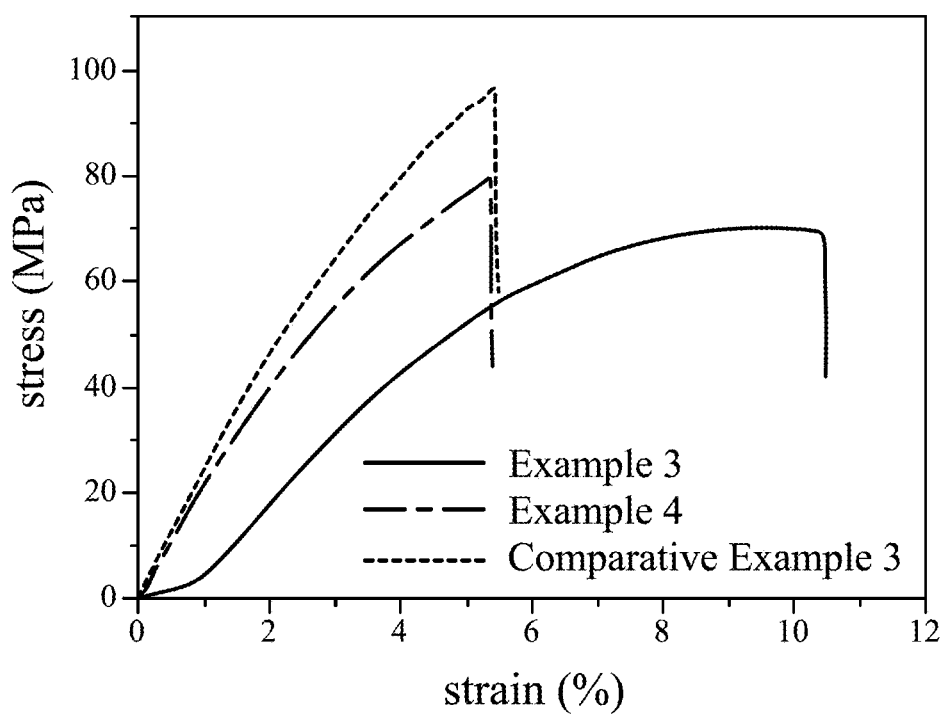
FIG. 13A is a stress-strain diagram of Example 3, Example 4 and Comparative Example 3.
Figure 13B:
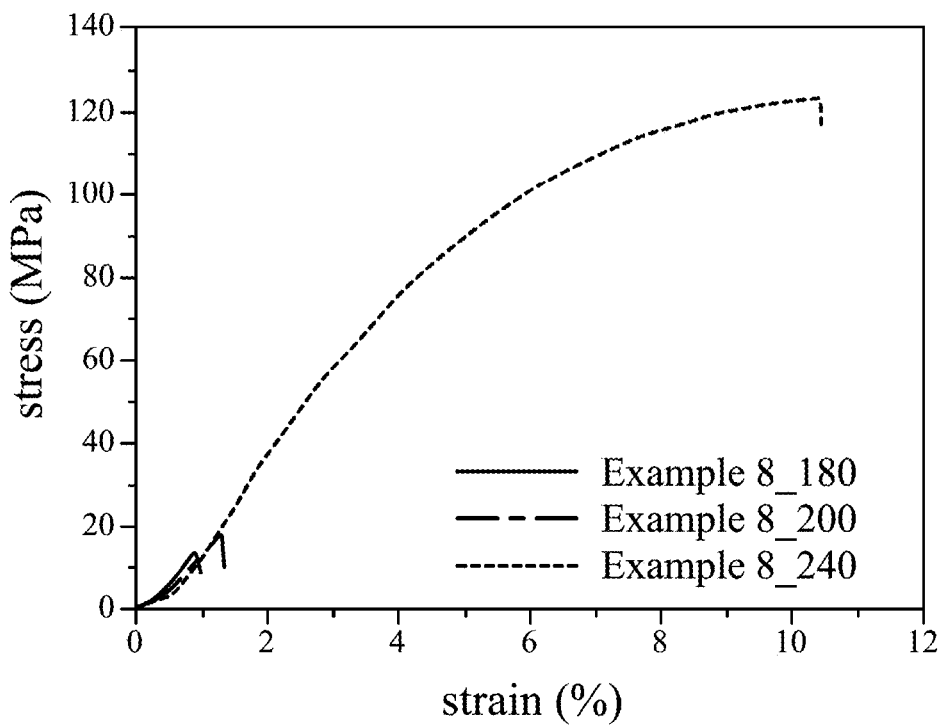
FIG. 13B is a stress-strain diagram of Example 8_180, Example 8_200 and Example 8_240.
Figure 13C:
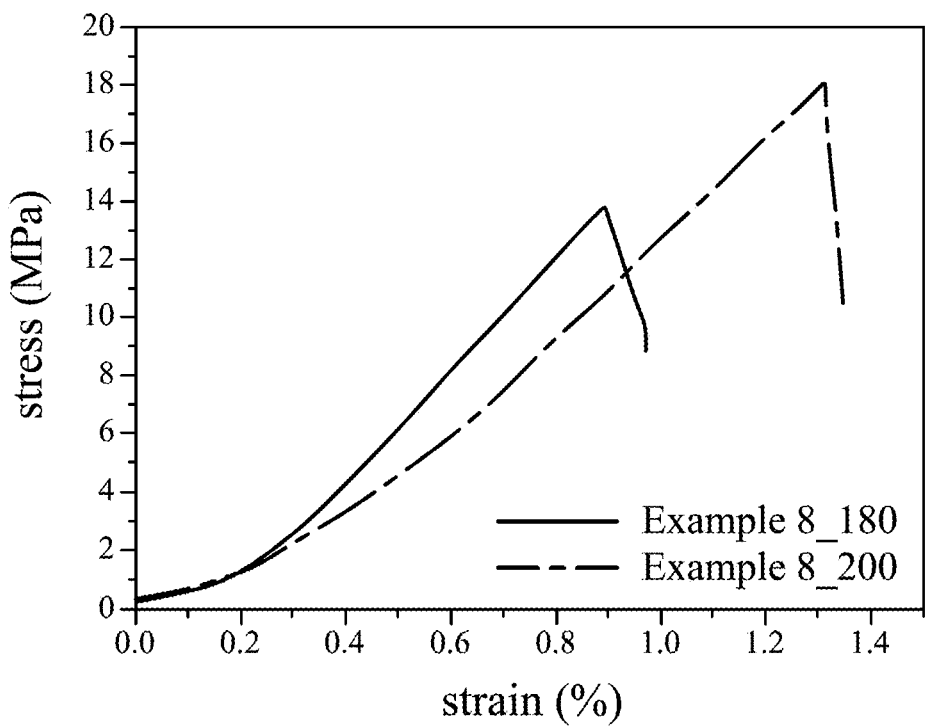
FIG. 13C is a stress-strain diagram of Example 8_180 and Example 8_200.
Figure 13D:
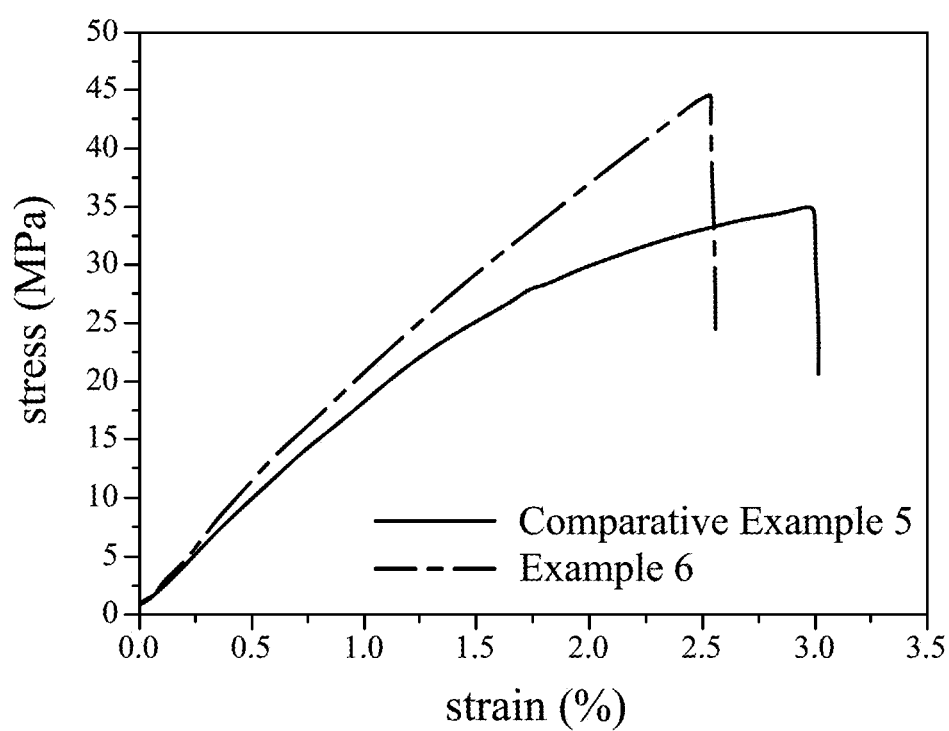
FIG. 13D is a stress-strain diagram of Example 6 and Comparative Example 5.

Example 3, Example 4, Example 6, Example 8, Comparative Example 3 and Comparative Example 5 are performed the tensile strength analysis to measure the mechanical property. Please refer to FIGS. 13A, 13B, 13C and 13D. FIG. 13A is a stress-strain diagram of Example 3, Example 4 and Comparative Example 3. FIG. 13B is a stress-strain diagram of Example 8_180, Example 8_200 and Example 8_240. FIG. 13C is a stress-strain diagram of Example 8_180 and Example 8_200. FIG. 13D is a stress-strain diagram of Example 6 and Comparative Example 5.

The stress, the strain and the Young's modulus of Example 3, Example 4, Example 6, Example 8, Comparative Example 3 and Comparative Example 5 are known by tensile strength analysis. The measurement results are shown in Table 10.

TABLE 10

|  | Stress (MPa) | Strain (%) | Young's modulus (MPa) |
| --- | --- | --- | --- |
| Example 3 | 70.92 ± 3.65 | 9.81 ± 0.36 | 1871.97 ± 38.18 |
| Example 4 | 81.49 ± 2.10 | 6.14 ± 0.25 | 2367.25 ± 123.36 |
| Comparative Example 3 | 97.68 ± 8.76 | 5.87 ± 0.48 | 2543.12 ± 93.84 |
| Example 6 | 44.35 ± 3.15 | 2.31 ± 0.54 | 2258.77 ± 97.21 |
| Comparative Example 5 | 35.56 ± 2.99 | 3.25 ± 1.09 | 2002.39 ± 251.43 |
| Example 8_180 | 13.25 ± 1.37 | 1.10 ± 0.11 | 785.53 ± 170.96 |
| Example 8_200 | 18.03 ± 2.67 | 1.18 ± 0.28 | 2214.38 ± 349.64 |
| Example 8_240 | 116.51 ± 8.40 | 10.00 ± 1.01 | 2737.86 ± 443.04 |

Optical Property Measurement

Figure 14:
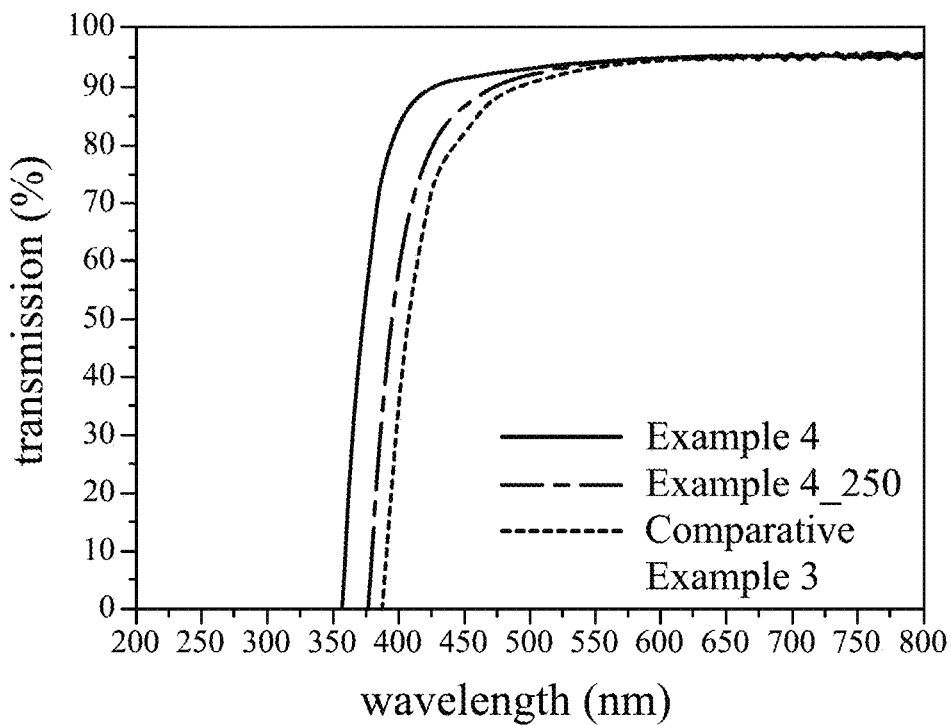
FIG. 14 is an UV spectrum of Example 4, Example 4_250 and Comparative Example 3.
Figure 15:
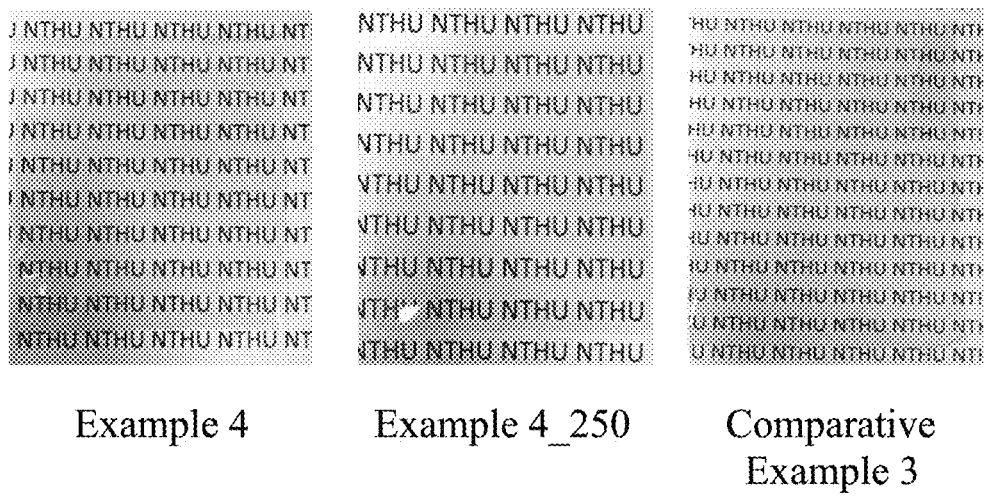
FIG. 15 is a diagram of the film of Example 4, Example 4_250 and Comparative Example 3.

Example 4 and Comparative Example 3 are performed the UV spectroscopy. Please refer to FIGS. 14 and 15, wherein FIG. 14 is an UV spectrum of Example 4, Example 4_250 and Comparative Example 3. FIG. 15 is a diagram of the film of Example 4, Example 4_250 and Comparative Example 3. The light transmittance ($T_\lambda$) and the cutoff wavelength ($\lambda$) of Example 4 and Comparative Example 3 are known by the UV spectroscopy. The measurement results are shown in Table 11.

TABLE 11

|  | $T_{400}$ (%) | $T_{450}$ (%) | $\lambda$(nm) |
| --- | --- | --- | --- |
| Example 4 | 83.2 | 91.4 | 356 |
| Example 4_250 | 58.1 | 86.6 | 376 |
| Comparative Example 3 | 36.8 | 81.9 | 388 |

As known in FIGS. 14 and 15, the shorter the cutoff wavelength, the lighter the film color, and is suitable for application to the photoelectric products.

In conclusion, the polymer prepared by the diamine compound having the Meldrum's acid structure has the high glass transition temperature and the characteristics of the thermal stability, the mechanical strength and the high light transmittance. It can improve the processability and the applicability of the polymer, and is suitable as the precursor to develop the high performance polymer materials and applied for the electronic components or 5G industries.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A diamine compound, comprising a structure represented by formula (I):

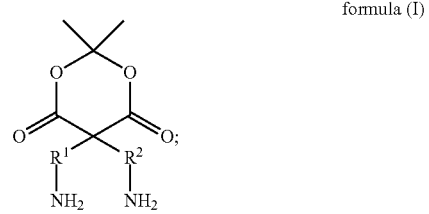

formula (I)

wherein $R^1$ and $R^2$ are the same or different from each other, and each independently an ether group, an ester group, an amine group or other heteroatom chains, a substituted or an unsubstituted alkyl group of 1 to 60 carbon atoms, a substituted or an unsubstituted alkenyl group of 2 to 60 carbon atoms, a substituted or an unsubstituted alkynyl group of 2 to 60 carbon atoms, a substituted or an unsubstituted aryl group of 6 to 30 carbon atoms or other carbon chains.

2. The diamine compound of claim 1, wherein in the formula (I), $R^1$ and $R^2$ are benzyl groups.

3. An amide bond-containing polymer material prepared by a ring-opening self-polymerization of the diamine compound of claim 1.

4. A polyimide prepared by a condensation reaction of the diamine compound of claim 1 and a dianhydride monomer.

5. The polyimide of claim 4, wherein the dianhydride monomer comprises a structure represented by formula (A):

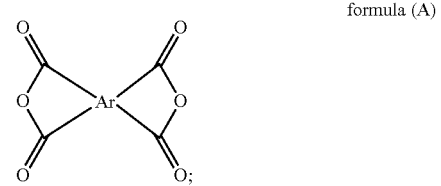

formula (A)

wherein Ar is a structure represented by formula (A-1), formula (A-2) or formula (A-3):

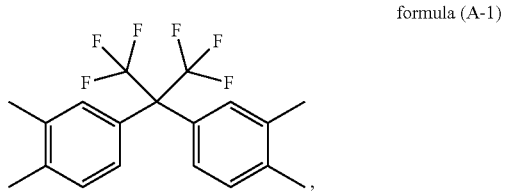

formula (A-1)

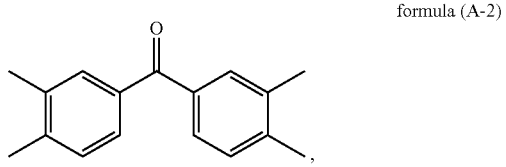

formula (A-2)

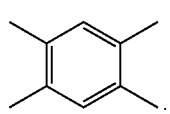

formula (A-3)

6. A polybenzoxazine prepared by a condensation reaction of the diamine compound of claim 1, a diphenol monomer and polyoxymethylene.

7. The polybenzoxazine of claim 6, wherein the diphenol monomer comprises a structure represented by formula (B):

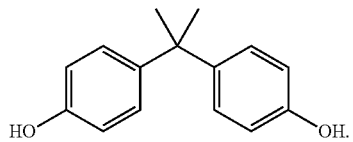

formula (B)

8. A thermosetting resin prepared by self-crosslinking of the diamine compound of claim 1.

9. A copolymerized thermosetting resin prepared by adding the diamine compound of claim 1 to a thermosetting resin system.

10. The copolymerized thermosetting resin of claim 9, wherein the thermosetting resin system is epoxy resin, phenolic resin, polyester resin, benzoxazine resin, carbamide resin or polyurethane resin.

\* \* \* \* \*

UNITED STATES PATENT AND TRADEMARK OFFICE
CERTIFICATE OF CORRECTION

PATENT NO. : 11,390,598 B2
APPLICATION NO. : 16/720488
DATED : July 19, 2022
INVENTOR(S) : Ying-Ling Liu et al.

It is certified that error appears in the above-identified patent and that said Letters Patent is hereby corrected as shown below:

On the Title Page

Column 2, Item (56) Other Publications, Line 1, delete "Wu etal" and insert -- Wu et al --

Column 2, Item (56) Other Publications, Line 5, delete "strucure" and insert -- structure --

Signed and Sealed this
Eighteenth Day of October, 2022

Katherine Kelly Vidal
*Director of the United States Patent and Trademark Office*